United States Patent
Boddepalli et al.

(10) Patent No.: US 9,982,271 B2
(45) Date of Patent: May 29, 2018

(54) CONTROLLING GENE EXPRESSION IN PLANTS USING FUSION PROTEIN CONTAINING LEXA BINDING DOMAIN AND DREB TRANSACTIVATION DOMAIN

(71) Applicant: E. I. DU PONT DE NEMOURS AND COMPANY, Wilmington, DE (US)

(72) Inventors: Janardhana Rao Boddepalli, Secunderabad (IN); Amitabh Mohanty, Secunderabad (IN); Michelle Oscar, Hyderabad (IN); Sriram Parameswaran, Bengalura (IN)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days. days.

(21) Appl. No.: 14/422,187

(22) PCT Filed: Aug. 20, 2013

(86) PCT No.: PCT/US2013/055791
§ 371 (c)(1),
(2) Date: Feb. 18, 2015

(87) PCT Pub. No.: WO2014/031643
PCT Pub. Date: Feb. 27, 2014

(65) Prior Publication Data
US 2015/0218572 A1    Aug. 6, 2015

Related U.S. Application Data

(60) Provisional application No. 61/715,479, filed on Oct. 18, 2012.

(30) Foreign Application Priority Data

Aug. 21, 2012 (IN) .......................... 2583/DEL//2012

(51) Int. Cl.
*C12N 15/82* (2006.01)
*C07K 14/415* (2006.01)
*C12N 15/62* (2006.01)

(52) U.S. Cl.
CPC ........ *C12N 15/8222* (2013.01); *C07K 14/415* (2013.01); *C12N 15/62* (2013.01); *C12N 15/8217* (2013.01)

(58) Field of Classification Search
None
See application file for complete search history.

(56) References Cited

U.S. PATENT DOCUMENTS 6,252,136 B1   6/2001  Bujard et al.
6,946,586 B1   9/2005  Fromm et al.
7,285,416 B2  10/2007  Choo et al.

FOREIGN PATENT DOCUMENTS

EP   0589841   4/2005

OTHER PUBLICATIONS

Liu et al. Two transcription factors, DREB1 and DREB2, with an EREBP/AP2 DNA binding domain separate two cellular signal transduction pathways in drought- and low-temperature-responsive gene expression, respectively, in *Arabidopsis*. (1998) vol. 10; pp. 1391-1406.*
Liu et al. Two transcription factors, DREB1 and DREB2, with an EREBP/AP2 DNA binding domain separate two cellular signal transduction pathways in dought- and low-temperature-responsive gene expression, respectively, in *Arabidopsis*. (1998) The Plant Cell; vol. 10; pp. 1391-1406.*
Uhlin et al. Nucleotide sequence of a recA operator mutation lexA/operator-repressor binding/inducible repair. (1982) Mol. Gen. Genet.; vol. 185; pp. 251-254.*
Lee et al. Functional characterization of NtCEF1, and AP2/EREBP-type transcriptional activator highly expressed in tobacco callus. (2005) Planta; vol. 222; pp. 211-224.*
Zuo et al. An estrogen receptor-based transactivator XVE mediates highly inducible gene expression in transgenic plants. (2000) The Plant Journal; vol. 24; pp. 265-273.*
Butala et al. The bacterial LexA transcriptional repressor. (2009) Cell. Mol. Life Sci.; vol. 66; pp. 82-93.*
Frankel et al. Modular structure of transcription factors: implications for gene regulation. (1991) Cell; vol. 65; pp. 717-719.*
Dmitrova et al. A new LexA-based genetic system for monitoring and analyzing protein heterodimerization in *Escherichia coli*. (1998 ) Mol. Gen. Genet.; vol. 257; pp. 205-212.*
International Search Report for PCT/US2013/055791, dated Nov. 28, 2013.
Stephen Rutherford, Federica Brandizzi, Helen Townley, Judith Craft, Yibing Wang, Ian Jepson, Alberto Martinez and Ian Moore. "Improved transcriptional activators and their use in mis-expression traps in *Arabidopsis*." The Plant Journal ,2005) 43, 769-788.
Ian Moore, Marketa Samalova and Smita Kurup. "Transactivated and chemically inducible gene expression in plants." The Plant Journal (2006) 45, 651-683.
Jia H, Van Loock B, Liao M, Verbelen JP, Vissenberg K. "Combination of the ALCR/alcA ethanol switch and GAL4/VP16-UAS enhancer trap system enables spatial and temporal control of transgene expression in *Arabidopsis*." Plant Biotechnol J. 2007 Jul;5(4):477-82.
Pascale Oertel-Buchheit, Dominique Porte, Manfred Schnarr and Michele Granger-Schnarrt. "Isolation and characterization of LexA mutant repressers with enhanced DNA binding affinity." J Mol. Biol. (1992) 225:609-620.
Roland Lloubes, Claude Lazdunski, Michele Granger-Schnarr1 and Manfred Schnar1. "DNA sequence determinants of LexA-induced DNA bending". Nucleic Acids Research, 1993, vol. 21, No. 10 2363-2367.
Coustry, Francoise et al. "Studies on Transcription Activation by the Multimeric CCAAT-binding Factor CBF" Journal of Biological Chemistry. 1995. vol. 270, No. 1, 468-475.

(Continued)

*Primary Examiner* — Cathy Kingdon Worley

(57) ABSTRACT

The present invention relates to the regulation of transgene expression in plants through a transactivation system which comprises the following: (1) a promoter comprising LexA binding sites; and (2) a fusion transactivator protein comprising a LexA DNA-binding domain and an activation domain, such as the transactivation domain of a C-repeat binding factor protein, for example, from a dehydration responsive element (DREB) factor.

17 Claims, 5 Drawing Sheets

(56) References Cited

OTHER PUBLICATIONS

International Preliminary Report on Patentability dated Feb. 24, 2015.
Weinmann, Pamela et al. "A chimeric transactivator allows tetracycline-responsive gene expression in whole plants." The Plant Journal. 1994. vol. 5. No. 4. 559-569.

* cited by examiner

SEQUENCE LISTING

<160> NUMBER OF SEQ ID NOS: 100

<210> SEQ ID NO 1
<211> LENGTH: 20
<212> TYPE: DNA
<213> ORGANISM: Artificial Sequence
<220> FEATURE:
<223> OTHER INFORMATION: fwd primer FL LexA

<400> SEQUENCE: 1
gaattcgata aatctctggt                                           20

<210> SEQ ID NO 2
<211> LENGTH: 20
<212> TYPE: DNA
<213> ORGANISM: Artificial Sequence
<220> FEATURE:
<223> OTHER INFORMATION: rev primer FL LexA

<400> SEQUENCE: 2
agctggtccg ccgttgcgcc                                           20

<210> SEQ ID NO 3
<211> LENGTH: 20
<212> TYPE: DNA
<213> ORGANISM: Artificial Sequence
<220> FEATURE:
<223> OTHER INFORMATION: fwd primer LexA ORF

<400> SEQUENCE: 3
atgaaagcgt taacggccag                                           20

<210> SEQ ID NO 4
<211> LENGTH: 20
<212> TYPE: DNA
<213> ORGANISM: Artificial Sequence
<220> FEATURE:
<223> OTHER INFORMATION: rev primer LexA ORF

<400> SEQUENCE: 4
ttacagccag tcgccgttgc                                           20

<210> SEQ ID NO 5
<211> LENGTH: 22
<212> TYPE: DNA
<213> ORGANISM: Artificial Sequence
<220> FEATURE:
<223> OTHER INFORMATION: fwd primer AtCBF1

<400> SEQUENCE: 5
agatataaat agctttacca ag                                        22

<210> SEQ ID NO 6
<211> LENGTH: 20
<212> TYPE: DNA
<213> ORGANISM: Artificial Sequence
<220> FEATURE:
<223> OTHER INFORMATION: rev primer AtCBF1

<400> SEQUENCE: 6
tattttccac tcgtttctac                                           20

<210> SEQ ID NO 7
<211> LENGTH: 22
<212> TYPE: DNA
<213> ORGANISM: Artificial Sequence

```
<220> FEATURE:
<223> OTHER INFORMATION: fwd primer CBF3/ DREB1a

<400> SEQUENCE: 7
agatctttta gttaccttat cc                                              22

<210> SEQ ID NO 8
<211> LENGTH: 24
<212> TYPE: DNA
<213> ORGANISM: Artificial Sequence
<220> FEATURE:
<223> OTHER INFORMATION: rev primer AtCBF3/DREB1a

<400> SEQUENCE: 8
taaaaagtat cgtactaaaa atgg                                            24

<210> SEQ ID NO 9
<211> LENGTH: 946
<212> TYPE: DNA
<213> ORGANISM: Arabidopsis thaliana

<400> SEQUENCE: 9
cttgaaaaag aatctacctg aaagaaaaa aagagagag agatataaat agctttacca       60
agacagatat actatctttt attaatccaa aaagactgag aactctagta actacgtact    120
acttaaacct tatccagttt cttgaaacag agtactctga tcaatgaact cattttcagc    180
tttttctgaa atgtttggct ccgattacga gcctcaaggc ggagattatt gtccgacgtt    240
ggccacgagt tgtccgaaga aaccggcggg ccgtaagaag tttcgtgaga ctcgtcaccc    300
aatttacaga ggagttcgtc aaagaaactc cggtaagtgg gtttctgaag tgagagagcc    360
aaacaagaaa accaggattt ggctcgggac tttccaaacc gctgagatgg cagctcgtgc    420
tcacgacgtc gctgcattag ccctccgtgg ccgatcagca tgtctcaact tcgctgactc    480
ggcttggcgg ctacgaatcc cggagtcaac atgcgccaag gatatccaaa aagcggctgc    540
tgaagcggcg ttggcttttc aagatgagac gtgtgatacg acgaccacga atcatggcct    600
ggacatggag gagacgatgg tggaagctat ttatacaccg aacagagcg aaggtgcgtt    660 ttatatggat gaggagacaa tgtttgggat gccgactttg ttggataata tggctgaagg    720 catgcttta ccgccgccgt ctgttcaatg gaatcataat tatgacggcg aaggagatgg    780
tgacgtgtcg ctttggagtt actaatattc gatagtcgtt tccattttg tactatagtt    840 tgaaaatatt ctagttcctt tttttagaat ggttccttca ttttattta ttttattgtt    900 gtagaaacga gtggaaaata attcaataca aaacaaatcg ttttct                   946

<210> SEQ ID NO 10
<211> LENGTH: 643
<212> TYPE: DNA
<213> ORGANISM: Arabidopsis thaliana

<400> SEQUENCE: 10
atgaactcat tttcagcttt ttctgaaatg tttggctccg attacgagcc tcaaggcgga    60
gattattgtc cgacgttggc cacgagttgt ccgaagaaac cggcgggccg taagaagttt    120
cgtgagactc gtcacccaat ttacagagga gttcgtcaaa gaaactccgg taagtgggtt    180
tctgaagtga gagagccaaa caagaaaacc aggatttggc tcgggacttt ccaaaccgct    240
gagatggcag ctcgtgctca cgacgtcgct gcattagccc tccgtggccg atcagcatgt    300
ctcaacttcg ctgactcggc ttggcggcta cgaatcccgg agtcaacatg cgccaaggat    360
```

```
atccaaaaag cggctgctga agcggcgttg gcttttcaag atgagacgtg tgatacgacg      420
accacgaatc atggcctgga catggaggag acgatggtgg aagctattta tacaccggaa      480
cagagcgaag gtgcgtttta tatggatgag agacaatgt ttgggatgcc gactttgttg      540
gataatatgg ctgaaggcat gcttttaccg ccgccgtctg ttcaatggaa tcataattat      600
gacggcgaag gagatggtga cgtgtcgctt tggagttact aat                       643
```

<210> SEQ ID NO 11
<211> LENGTH: 213
<212> TYPE: PRT
<213> ORGANISM: Arabidopsis thaliana

<400> SEQUENCE: 11

```
Met Asn Ser Phe Ser Ala Phe Ser Glu Met Phe Gly Ser Asp Tyr Glu
1               5                   10                  15

Pro Gln Gly Gly Asp Tyr Cys Pro Thr Leu Ala Thr Ser Cys Pro Lys
            20                  25                  30

Lys Pro Ala Gly Arg Lys Phe Arg Glu Thr Arg His Pro Ile Tyr
        35                  40                  45

Arg Gly Val Arg Gln Arg Asn Ser Gly Lys Trp Val Ser Glu Val Arg
    50                  55                  60

Glu Pro Asn Lys Lys Thr Arg Ile Trp Leu Gly Thr Phe Gln Thr Ala
65                  70                  75                  80

Glu Met Ala Ala Arg Ala His Asp Val Ala Ala Leu Ala Leu Arg Gly
                85                  90                  95

Arg Ser Ala Cys Leu Asn Phe Ala Asp Ser Ala Trp Arg Leu Arg Ile
            100                 105                 110

Pro Glu Ser Thr Cys Ala Lys Asp Ile Gln Lys Ala Ala Ala Glu Ala
        115                 120                 125

Ala Leu Ala Phe Gln Asp Glu Thr Cys Asp Thr Thr Thr Asn His
    130                 135                 140

Gly Leu Asp Met Glu Glu Thr Met Val Glu Ala Ile Tyr Thr Pro Glu
145                 150                 155                 160

Gln Ser Glu Gly Ala Phe Tyr Met Asp Glu Glu Thr Met Phe Gly Met
                165                 170                 175

Pro Thr Leu Leu Asp Asn Met Ala Glu Gly Met Leu Leu Pro Pro Pro
            180                 185                 190

Ser Val Gln Trp Asn His Asn Tyr Asp Gly Glu Gly Asp Gly Asp Val
        195                 200                 205

Ser Leu Trp Ser Tyr
    210
```

<210> SEQ ID NO 12
<211> LENGTH: 651
<212> TYPE: DNA
<213> ORGANISM: Arabidopsis thaliana

<400> SEQUENCE: 12

```
atgaactcat tttctgcttt ttctgaaatg tttggctccg attacgagtc ttcggtttcc       60
tcaggcggtg attatattcc gacgcttgcg agcagctgcc ccaagaaacc ggcgggtcgt      120
aagaagtttc gtgagactcg tcacccaata tacagaggag ttcgtcggag aaactccggt      180
aagtgggttt gtgaggttag agaaccaaac aagaaaacaa ggatttggct cggaacattt      240
caaaccgctg agatggcagc tcgagctcac gacgttgccg ctttagccct tcgtggccga      300
tcagcctgtc tcaatttcgc tgactcggct tggagactcc gaatcccgga atcaacttgc      360
```

```
gctaaggaca tccaaaaggc ggcggctgaa gctgcgttgg cgtttcagga tgagatgtgt    420
gatgcgacga cggatcatgg cttcgacatg gaggagacgt tggtggaggc tatttacacg    480
gcggaacaga gcgaaaatgc gttttatatg cacgatgagg cgatgtttga tgccgagt     540 ttgttggcta atatggcaga agggatgctt ttgccgcttc cgtccgtaca gtggaatcat    600
aatcatgaag tcgacggcga tgatgacgac gtatcgttat ggagttatta a            651
```

```
<210> SEQ ID NO 13
<211> LENGTH: 216
<212> TYPE: PRT
<213> ORGANISM: Arabidopsis thaliana

<400> SEQUENCE: 13
```

```
Met Asn Ser Phe Ser Ala Phe Ser Glu Met Phe Gly Ser Asp Tyr Glu
1               5                   10                  15

Ser Ser Val Ser Ser Gly Gly Asp Tyr Ile Pro Thr Leu Ala Ser Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Arg Arg Asn Ser Gly Lys Trp Val Cys
    50                  55                  60

Glu Val Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Asp Ile Gln Lys Ala Ala
        115                 120                 125

Ala Glu Ala Ala Leu Ala Phe Gln Asp Glu Met Cys Asp Ala Thr Thr
    130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
            180                 185                 190

Leu Pro Ser Val Gln Trp Asn His Asn His Glu Val Asp Gly Asp Asp
        195                 200                 205

Asp Asp Val Ser Leu Trp Ser Tyr
    210                 215
```

```
<210> SEQ ID NO 14
<211> LENGTH: 609
<212> TYPE: DNA
<213> ORGANISM: Escherichia coli

<400> SEQUENCE: 14
```

```
atgaaagcgt taacggccag caacaagag gtgtttgatc tcatccgtga tcacatcagc     60
cagacaggta tgccgccgac gcgtgcggaa atcgcgcagc gtttgggggtt ccgttcccca   120 aacgcggctg aagaacatct gaaggcgctg gcacgcaaag gcgttattga aattgtttcc   180
ggcgcatcac gcgggattcg tctgttgcag gaagaggaag aagggttgcc gctggtaggt   240
cgtgtggctg ccggtgaacc acttctggcg caacagcata ttgaaggtca ttatcaggtc   300
```

```
gatccttcct tattcaagcc gaatgctgat ttcctgctgc gcgtcagcgg gatgtcgatg    360
aaagatatcg gcattatgga tggtgacttg ctggcagtgc ataaaactca ggatgtacgt    420
aacggtcagg tcgttgtcgc acgtattgat gacgaagtta ccgttaagcg cctgaaaaaa    480
cagggcaata agtcgaact gttgccagaa aatagcgagt ttaaaccaat tgtcgttgac    540
cttcgtcagc agagcttcac cattgaaggg ctggcggttg gggttattcg caacggcgac    600
tggctgtaa                                                            609
```

<210> SEQ ID NO 15
<211> LENGTH: 202
<212> TYPE: PRT
<213> ORGANISM: Escherichia coli

<400> SEQUENCE: 15

```
Met Lys Ala Leu Thr Ala Arg Gln Gln Glu Val Phe Asp Leu Ile Arg
 1               5                  10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200
```

<210> SEQ ID NO 16
<211> LENGTH: 82
<212> TYPE: DNA
<213> ORGANISM: Cauliflower mosaic virus

<400> SEQUENCE: 16

```
caatcccact atccttcgca agaccttcc tctatataag gaagttcatt tcatttggag    60
aggacacgca tatgaaatca cc                                             82
```

<210> SEQ ID NO 17
<211> LENGTH: 67
<212> TYPE: DNA
<213> ORGANISM: Tobacco mosaic virus

<400> SEQUENCE: 17

```
tatttttaca acaattacca acaacaacaa acaacaaaca acattacaat tactatttac      60
aattaca                                                                67

<210> SEQ ID NO 18
<211> LENGTH: 85
<212> TYPE: DNA
<213> ORGANISM: Artificial Sequence
<220> FEATURE:
<223> OTHER INFORMATION: minicorpromU oligonulceotide

<400> SEQUENCE: 18
caatcccact atccttcgca agacccttcc tctatataag gaagttcatt tcatttggag      60
aggacacgca tatgaaatca cctat                                            85

<210> SEQ ID NO 19
<211> LENGTH: 84
<212> TYPE: DNA
<213> ORGANISM: Artificial Sequence
<220> FEATURE:
<223> OTHER INFORMATION: minicorepromL oligo

<400> SEQUENCE: 19
tgtaattgta aatagtaatt gtaatgttgt tgttgtttg ttgttgttgg taattgttgt       60
aaaaataggt gatttcatat gcgt                                             84

<210> SEQ ID NO 20
<211> LENGTH: 952
<212> TYPE: DNA
<213> ORGANISM: Escherichia coli

<400> SEQUENCE: 20
gaattcgata atctctggt ttattgtgca gtttatggtt ccaaaatcgc cttttgctgt       60
atatactcac agcataactg tatatacacc caggggggcgg aatgaaagcg ttaacggcca   120
ggcaacaaga ggtgtttgat ctcatccgtg atcacatcag ccagacaggt atgccgccga    180
cgcgtgcgga atcgcgcag cgtttggggt tccgttcccc aaacgcggct gaagaacatc    240
tgaaggcgct ggcacgcaaa ggcgttattg aaattgtttc cggcgcatca cgcgggattc    300
gtctgttgca ggaagaggaa gaagggttgc cgctggtagg tcgtgtggct gccggtgaac    360
cacttctggc gcaacagcat attgaaggtc attatcaggt cgatccttcc ttattcaagc    420
cgaatgctga tttcctgctg cgcgtcagcg ggatgtcgat gaaagatatc ggcattatgg    480
atggtgactt gctggcagtg cataaaactc aggatgtacg taacggtcag gtcgttgtcg    540
cacgtattga tgacgaagtt accgttaagc gcctgaaaaa acagggcaat aaagtcgaac    600
tgttgccaga aaatagcgag tttaaaccaa ttgtcgttga ccttcgtcag cagagcttca    660
ccattgaagg gctggcggtt ggggttattc gcaacggcga ctggctgtaa catatctctg    720
agaccgcgat gccgcctggc gtcgcggttt gttttttcatc tctcttcatc aggcttgtct    780
gcatggcatt cctcacttca tctgataaag cactctggca tctcgcctta cccatgattt    840
tctccaatat caccgttccg ttgctgggac tggtcgatac ggcggtaatt ggtcatcttg    900
atagcccggt ttatttgggc ggcgtggcgg ttggcgcaac ggcggaccag ct            952

<210> SEQ ID NO 21
<211> LENGTH: 149
<212> TYPE: DNA
<213> ORGANISM: Artificial Sequence
<220> FEATURE:
<223> OTHER INFORMATION: CMV promoter-TMV omega
```

```
<400> SEQUENCE: 21
caatcccact atccttcgca agacccttcc tctatataag gaagttcatt tcatttggag      60
aggacacgca tatgaaatca cctattttta caacaattac caacaacaac aaacaacaaa     120
caacattaca attactattt acaattaca                                       149

<210> SEQ ID NO 22
<211> LENGTH: 51
<212> TYPE: DNA
<213> ORGANISM: Artificial Sequence
<220> FEATURE:
<223> OTHER INFORMATION: RecA op

<400> SEQUENCE: 22
gatactgtat atactcacag tatcatatga tactgtatat actcacagta t              51

<210> SEQ ID NO 23
<211> LENGTH: 94
<212> TYPE: DNA
<213> ORGANISM: Artificial Sequence
<220> FEATURE:
<223> OTHER INFORMATION: Caa operator

<400> SEQUENCE: 23
caaaaactgt tatataacac atgtgttata taacagtaaa aatgatgatc caaaaactgt      60
atatattcac atgtgtttat atacagtaaa atga                                 94

<210> SEQ ID NO 24
<211> LENGTH: 181
<212> TYPE: DNA
<213> ORGANISM: Artificial Sequence
<220> FEATURE:
<223> OTHER INFORMATION: RecA-Caa operator hybrid

<400> SEQUENCE: 24
aattcgccct tcaaaaactg ttatataaca catgtgttat ataacagtaa aaatgatgat      60
ccaaaaactg tatatattca catgtgttta tatacagtaa aatgaaaggg cgaattcgcc     120
cttgatactg tatatactca cagtatcata tgatactgta tatactcaca gtataagggc     180
g                                                                    181

<210> SEQ ID NO 25
<211> LENGTH: 51
<212> TYPE: DNA
<213> ORGANISM: Artificial Sequence
<220> FEATURE:
<223> OTHER INFORMATION: recAop upperoligo

<400> SEQUENCE: 25
gatactgtat atactcacag tatcatatga tactgtatat actcacagta t              51

<210> SEQ ID NO 26
<211> LENGTH: 51
<212> TYPE: DNA
<213> ORGANISM: Artificial Sequence
<220> FEATURE:
<223> OTHER INFORMATION: recAopL

<400> SEQUENCE: 26
atactgtgag tatatacagt atcatatgat actgtgagta tatacagtat c              51

<210> SEQ ID NO 27
```

<210> SEQ ID NO 27
<211> LENGTH: 59
<212> TYPE: DNA
<213> ORGANISM: Artificial Sequence
<220> FEATURE:
<223> OTHER INFORMATION: CaaopU oligonucleotide

<400> SEQUENCE: 27
tcattttact gtatataaac acatgtgaat atatacagtt tttggatcat cattttta c    59

<210> SEQ ID NO 28
<211> LENGTH: 59
<212> TYPE: DNA
<213> ORGANISM: Artificial Sequence
<220> FEATURE:
<223> OTHER INFORMATION: CaaopL oligonucleotide

<400> SEQUENCE: 28
caaaaactgt tataacac atgtgttata taacagtaaa aatgatgatc caaaaactg    59

<210> SEQ ID NO 29
<211> LENGTH: 56
<212> TYPE: DNA
<213> ORGANISM: Artificial Sequence
<220> FEATURE:
<223> OTHER INFORMATION: HybopUhalf oligonucleotide

<400> SEQUENCE: 29
gggaattcta tcattttact gtatataaac acatgtgaat atacagtttt tggtgg    56

<210> SEQ ID NO 30
<211> LENGTH: 56
<212> TYPE: DNA
<213> ORGANISM: Artificial Sequence
<220> FEATURE:
<223> OTHER INFORMATION: HybOpLhalf oligonucleotide

<400> SEQUENCE: 30
agggatccta tactgtatgc tcatacagta tcggcgcgcc accaaaaact gtatat    56

<210> SEQ ID NO 31
<211> LENGTH: 261
<212> TYPE: DNA
<213> ORGANISM: Artificial Sequence
<220> FEATURE:
<223> OTHER INFORMATION: LexA DNA-binding domain

<400> SEQUENCE: 31
atgaaagcgt taacggccag gcaacaagag gtgtttgatc tcatccgtga tcacatcagc     60
cagacaggta tgccgccgac gcgtgcggaa atcgcgcagc gtttggggtt ccgttcccca    120
aacgcggctg aagaacatct gaaggcgctg gcacgcaaag gcgttattga aattgtttcc    180
ggcgcatcac gcgggattcg tctgttgcag gaagaggaag aagggttgcc gctggtaggt    240
cgtgtggctg ccggtgaacc a                                              261

<210> SEQ ID NO 32
<211> LENGTH: 87
<212> TYPE: PRT
<213> ORGANISM: Artificial Sequence
<220> FEATURE:
<223> OTHER INFORMATION: LexA DBD

<400> SEQUENCE: 32

Met Lys Ala Leu Thr Ala Arg Gln Gln Glu Val Phe Asp Leu Ile Arg
 1               5                  10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro
                85

<210> SEQ ID NO 33
<211> LENGTH: 261
<212> TYPE: DNA
<213> ORGANISM: Artificial Sequence
<220> FEATURE:
<223> OTHER INFORMATION: LexA DBD mutNLS

<400> SEQUENCE: 33
atgaaagcgt taacggccag gcaacaagag gtgtttgatc tcatccgtga tcacatcagc    60
cagacaggta tgccgccgac gcgtgcggaa atcgcgcagc gtttgggggtt ccgttcccca   120 aacgcggctg aagaacatct gaaggcgctg gcacgcaaag gcgttattga aattgtttcc   180
ggcgcatcac gcgggattcg tctgttgcag gaagaggaag aagggttgcc gctggtaggt   240
cgtgtggctg ccgatgaacc a                                              261

<210> SEQ ID NO 34
<211> LENGTH: 87
<212> TYPE: PRT
<213> ORGANISM: Artificial Sequence
<220> FEATURE:
<223> OTHER INFORMATION: LexAMNF_aa

<400> SEQUENCE: 34

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Lys Glu Glu Glu Gly Leu Pro Leu Val Gly
65                  70                  75                  80

Arg Val Ala Ala Asp Glu Pro
                85

<210> SEQ ID NO 35
<211> LENGTH: 606
<212> TYPE: DNA
<213> ORGANISM: Artificial Sequence
<220> FEATURE:
<223> OTHER INFORMATION: LexA mutFL

<400> SEQUENCE: 35
atgaaagcgt taacggccag gcaacaagag gtgtttgatc tcatccgtga tcacatcagc    60
cagacaggta tgccgccgac gcgtgcggaa atcgcgcagc gtttgggggtt ccgttcccca   120 aacgcggctg aagaacatct gaaggcgctg gcacgcaaag gcgttattga aattgtttcc   180

```
ggcgcatcac gcgggattcg tctgttgcag gaagaggaag aagggttgcc gctggtaggt      240
cgtgtggctg ccgatgaacc acttctggcg caacagcata ttgaaggtca ttatcaggtc      300
gatccttcct tattcaagcc gaatgctgat ttcctgctgc gcgtcagcgg gatggcgatg      360
aaagacatcg gcattatgga tggtgacttg ctggcagtgc ataaaactca ggatgtacgt      420
aacggtcagg tcgttgtcgc acgtattgat gacgaagtta ccgttaagcg cctgaaaaaa      480
cagggcaata agtcgaact gttgccagaa aatagcgagt ttaaaccaat tgtcgttgac       540
cttcgtcagc agagcttcac cattgaaggg ctggcggttg gggttattcg caacggcgac      600
tggctg                                                                 606

<210> SEQ ID NO 36
<211> LENGTH: 202
<212> TYPE: PRT
<213> ORGANISM: Artificial Sequence
<220> FEATURE:
<223> OTHER INFORMATION: LexAFL_aa

<400> SEQUENCE: 36

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Asp Glu Pro Leu Leu Ala Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ala Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200

<210> SEQ ID NO 37
<211> LENGTH: 609
<212> TYPE: DNA
<213> ORGANISM: Artificial Sequence
<220> FEATURE:
<223> OTHER INFORMATION: LexAmut FL NLS

<400> SEQUENCE: 37
atgaaagcgt taacggccag gcaacaagag gtgtttgatc tcatccgtga tcacatcagc       60
cagacaggta tgccgccgac gcgtgcggaa atcgcgcagc gtttgggggtt ccgttcccca    120
```

```
aacgcggctg aagaacatct gaaggcgctg gcacgcaaag gcgttattga aattgtttcc      180
ggcgcatcac gcgggattcg tctgttgcag aaagaggaag aagggttgcc gctggtaggt      240
cgtgtggctg ccgatgaacc acttctggcg caacagcata ttgaaggtca ttatcaggtc      300
gatccttcca agaaacgcaa gccgaatgct gatttcctgc tgcgcgtcag cgggatggcg      360
atgaaagaca tcggcattat ggatggtgac ttgctggcag tgcataaaac tcaggatgta      420
cgtaacggtc aggtcgttgt cgcacgtatt gatgacgaag ttaccgttaa gcgcctgaaa      480
aaacagggca ataaagtcga actgttgcca gaaaatagcg agtttaaacc aattgtcgtt      540
gaccttcgtc agcagagctt caccattgaa gggctggcgg ttggggttat tcgcaacggc      600
gactggctg                                                              609
```

<210> SEQ ID NO 38
<211> LENGTH: 203
<212> TYPE: PRT
<213> ORGANISM: Artificial Sequence
<220> FEATURE:
<223> OTHER INFORMATION: LexAFLNLS

<400> SEQUENCE: 38

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Lys Glu Glu Gly Leu Pro Leu Val Gly
65                  70                  75                  80

Arg Val Ala Ala Asp Glu Pro Leu Leu Ala Gln Gln His Ile Glu Gly
                85                  90                  95

His Tyr Gln Val Asp Pro Ser Lys Lys Arg Lys Pro Asn Ala Asp Phe
            100                 105                 110

Leu Leu Arg Val Ser Gly Met Ala Met Lys Asp Ile Gly Ile Met Asp
        115                 120                 125

Gly Asp Leu Leu Ala Val His Lys Thr Gln Asp Val Arg Asn Gly Gln
    130                 135                 140

Val Val Val Ala Arg Ile Asp Asp Glu Val Thr Val Lys Arg Leu Lys
145                 150                 155                 160

Lys Gln Gly Asn Lys Val Glu Leu Leu Pro Glu Asn Ser Glu Phe Lys
                165                 170                 175

Pro Ile Val Val Asp Leu Arg Gln Gln Ser Phe Thr Ile Glu Gly Leu
            180                 185                 190

Ala Val Gly Val Ile Arg Asn Gly Asp Trp Leu
        195                 200
```

<210> SEQ ID NO 39
<211> LENGTH: 12
<212> TYPE: DNA
<213> ORGANISM: Artificial Sequence
<220> FEATURE:
<223> OTHER INFORMATION: NLS

<400> SEQUENCE: 39
aagaaacgca ag                                                          12

<210> SEQ ID NO 40
<211> LENGTH: 297
<212> TYPE: DNA
<213> ORGANISM: Artificial Sequence
<220> FEATURE:
<223> OTHER INFORMATION: AtCBF1 fragA

<400> SEQUENCE: 40
acatgcgcca aggatatcca aaaagcggct gctgaagcgg cgttggcttt tcaagatgag     60
acgtgtgata cgacgaccac gaatcatggc ctggacatgg aggagacgat ggtggaagct    120
atttatacac cggaacagag cgaaggtgcg ttttatatgg atgaggagac aatgtttggg    180
atgccgactt tgttggataa tatggctgaa ggcatgcttt taccgccgcc gtctgttcaa    240
tggaatcata attatgacgg cgaaggagat ggtgacgtgt cgctttggag ttactaa      297

<210> SEQ ID NO 41
<211> LENGTH: 261
<212> TYPE: DNA
<213> ORGANISM: Artificial Sequence
<220> FEATURE:
<223> OTHER INFORMATION: AtCBF1 fragB

<400> SEQUENCE: 41
acatgcgcca aggatatcca aaaagcggct gctgaagcgg cgttggcttt tcaagatgag     60
acgtgtgata cgacgaccac gaatcatggc ctggacatgg aggagacgat ggtggaagct    120
atttatacac cggaacagag cgaaggtgcg ttttatatgg atgaggagac aatgtttggg    180
atgccgactt tgttggataa tatggctgaa ggcatgcttt taccgccgcc gtctgttcaa    240
tggaatcata attatgacta a                                              261

<210> SEQ ID NO 42
<211> LENGTH: 225
<212> TYPE: DNA
<213> ORGANISM: Artificial Sequence
<220> FEATURE:
<223> OTHER INFORMATION: AtCBF fragC

<400> SEQUENCE: 42
acatgcgcca aggatatcca aaaagcggct gctgaagcgg cgttggcttt tcaagatgag     60
acgtgtgata cgacgaccac gaatcatggc ctggacatgg aggagacgat ggtggaagct    120
atttatacac cggaacagag cgaaggtgcg ttttatatgg atgaggagac aatgtttggg    180
atgccgactt tgttggataa tatggctgaa ggcatgcttt tataa                    225

<210> SEQ ID NO 43
<211> LENGTH: 189
<212> TYPE: DNA
<213> ORGANISM: Artificial Sequence
<220> FEATURE:
<223> OTHER INFORMATION: AtCBF1 fragD

<400> SEQUENCE: 43
acatgcgcca aggatatcca aaaagcggct gctgaagcgg cgttggcttt tcaagatgag     60
acgtgtgata cgacgaccac gaatcatggc ctggacatgg aggagacgat ggtggaagct    120
atttatacac cggaacagag cgaaggtgcg ttttatatgg atgaggagac aatgtttgga    180
atgccgtaa                                                            189

<210> SEQ ID NO 44
<211> LENGTH: 132

```
<212> TYPE: DNA
<213> ORGANISM: Artificial Sequence
<220> FEATURE:
<223> OTHER INFORMATION: AtCBF1 fragE

<400> SEQUENCE: 44
cccgaacaga gcgaaggtgc gttttatatg gatgaggaga caatgtttgg gatgccgact    60
ttgttggata atatggctga aggcatgctt ttaccgccgc cgtctgttca atggaatcat   120
aattatgact aa                                                       132

<210> SEQ ID NO 45
<211> LENGTH: 108
<212> TYPE: DNA
<213> ORGANISM: Artificial Sequence
<220> FEATURE:
<223> OTHER INFORMATION: AtCBF fragF

<400> SEQUENCE: 45
cccgaacaga gcgaaggtgc gttttatatg gatgaggaga caatgtttgg gatgccgact    60
ttgttggata atatggctga aggcatgctt ttaccgccgc cgtcttaa                108

<210> SEQ ID NO 46
<211> LENGTH: 159
<212> TYPE: DNA
<213> ORGANISM: Artificial Sequence
<220> FEATURE:
<223> OTHER INFORMATION: AtCBF fragG

<400> SEQUENCE: 46
agcgaaggtg cgttttatat ggatgaggag acaatgtttg ggatgccgac tttgttggat    60
aatatggctg aaggcatgct tttaccgccg ccgtctgttc aatggaatca taattatgac   120
ggcgaaggag atggtgacgt gtcgctttgg agttactaa                          159

<210> SEQ ID NO 47
<211> LENGTH: 213
<212> TYPE: DNA
<213> ORGANISM: Artificial Sequence
<220> FEATURE:
<223> OTHER INFORMATION: AtCBF3 fragI

<400> SEQUENCE: 47
ggcttcgaca tggaggagac gttggtggag gctatttaca cggcggaaca gagcgaaaat    60
gcgttttata tgcacgatga ggcgatgttt gagatgccga gtttgttggc taatatggca   120
gaagggatgc ttttgccgct tccgtccgta cagtggaatc ataatcatga agtcgacggc   180
gatgatgacg acgtatcgtt atggagttat taa                                213

<210> SEQ ID NO 48
<211> LENGTH: 30
<212> TYPE: DNA
<213> ORGANISM: Artificial Sequence
<220> FEATURE:
<223> OTHER INFORMATION: LexA fusion fwd primer

<400> SEQUENCE: 48
agactcgaga tgaaagcgtt aacggccagg                                     30

<210> SEQ ID NO 49
<211> LENGTH: 35
<212> TYPE: DNA
<213> ORGANISM: Artificial Sequence
<220> FEATURE:
```

<223> OTHER INFORMATION: CBF1 fragA fwd primer

<400> SEQUENCE: 49
ggcgcgcccg ggcccacatg cgccaaggat atcca                35

<210> SEQ ID NO 50
<211> LENGTH: 33
<212> TYPE: DNA
<213> ORGANISM: Artificial Sequence
<220> FEATURE:
<223> OTHER INFORMATION: CBF1 fragA and fragG rev primer

<400> SEQUENCE: 50
aacaagcttc attagtaact ccaaagcgac acg                  33

<210> SEQ ID NO 51
<211> LENGTH: 38
<212> TYPE: DNA
<213> ORGANISM: Artificial Sequence
<220> FEATURE:
<223> OTHER INFORMATION: CBF1 fragB rev primer

<400> SEQUENCE: 51
actaagcttc attagtcata attatgattc cattgaac             38

<210> SEQ ID NO 52
<211> LENGTH: 30
<212> TYPE: DNA
<213> ORGANISM: Artificial Sequence
<220> FEATURE:
<223> OTHER INFORMATION: CBF1 fragC rev primer

<400> SEQUENCE: 52
actaagctta taaaagcatg ccttcagcca              30

<210> SEQ ID NO 53
<211> LENGTH: 31
<212> TYPE: DNA
<213> ORGANISM: Artificial Sequence
<220> FEATURE:
<223> OTHER INFORMATION: CBF1_fragD rev primer

<400> SEQUENCE: 53
actaagctta cggcatccca aacattgtct c            31

<210> SEQ ID NO 54
<211> LENGTH: 35
<212> TYPE: DNA
<213> ORGANISM: Artificial Sequence
<220> FEATURE:
<223> OTHER INFORMATION: CBF1_fragE fwd primer

<400> SEQUENCE: 54
ggcgcgcccg ggcccgaaca gagcgaaggt gcgtt        35

<210> SEQ ID NO 55
<211> LENGTH: 30
<212> TYPE: DNA
<213> ORGANISM: Artificial Sequence
<220> FEATURE:
<223> OTHER INFORMATION: CBF1_FragF rev primer

<400> SEQUENCE: 55
actaagctta agacggcggc ggtaaaagca              30

<210> SEQ ID NO 56
<211> LENGTH: 36
<212> TYPE: DNA
<213> ORGANISM: Artificial Sequence
<220> FEATURE:
<223> OTHER INFORMATION: CBF1_fragG fwd primer

<400> SEQUENCE: 56
ggcgcgcccg ggcccagcga aggtgcgttt tatatg             36

<210> SEQ ID NO 57
<211> LENGTH: 39
<212> TYPE: DNA
<213> ORGANISM: Artificial Sequence
<220> FEATURE:
<223> OTHER INFORMATION: CBF3_fragI fwd primer

<400> SEQUENCE: 57
ggcgcgcccg ggcccggctt cgacatggag gagacgttg          39

<210> SEQ ID NO 58
<211> LENGTH: 36
<212> TYPE: DNA
<213> ORGANISM: Artificial Sequence
<220> FEATURE:
<223> OTHER INFORMATION: CBF3_FragI rev primer

<400> SEQUENCE: 58
aacaagcttc attaataact ccataacgat acgtcg             36

<210> SEQ ID NO 59
<211> LENGTH: 53
<212> TYPE: DNA
<213> ORGANISM: Artificial Sequence
<220> FEATURE:
<223> OTHER INFORMATION: LexAMNF-rev primer

<400> SEQUENCE: 59
gggcgcgccg cgcccacga ggcgcttctt ttttggttca tcggcagcca cac    53

<210> SEQ ID NO 60
<211> LENGTH: 35
<212> TYPE: DNA
<213> ORGANISM: Artificial Sequence
<220> FEATURE:
<223> OTHER INFORMATION: CBF1-fragA _fwd primer for MNF

<400> SEQUENCE: 60
ggcgccggcg cgcccacatg cgccaaggat atcca              35

<210> SEQ ID NO 61
<211> LENGTH: 33
<212> TYPE: DNA
<213> ORGANISM: Artificial Sequence
<220> FEATURE:
<223> OTHER INFORMATION: CBF1_A_rev primer_ for LexA MNF fusion

<400> SEQUENCE: 61
aacaagcttc attagtaact ccaaagcgac acg                33

<210> SEQ ID NO 62
<211> LENGTH: 38
<212> TYPE: DNA
<213> ORGANISM: Artificial Sequence
<220> FEATURE:
<223> OTHER INFORMATION: CBF1_B_revprimer_LexAMNF

<400> SEQUENCE: 62
actaagcttc attagtcata attatgattc cattgaac      38

<210> SEQ ID NO 63
<211> LENGTH: 30
<212> TYPE: DNA
<213> ORGANISM: Artificial Sequence
<220> FEATURE:
<223> OTHER INFORMATION: CBF1_C_revprimer_LexAMNF

<400> SEQUENCE: 63
actaagctta taaaagcatg ccttcagcca      30

<210> SEQ ID NO 64
<211> LENGTH: 31
<212> TYPE: DNA
<213> ORGANISM: Artificial Sequence
<220> FEATURE:
<223> OTHER INFORMATION: CBF1_D-revprimer_LexAMNF

<400> SEQUENCE: 64
actaagctta cggcatccca aacattgtct c      31

<210> SEQ ID NO 65
<211> LENGTH: 35
<212> TYPE: DNA
<213> ORGANISM: Artificial Sequence
<220> FEATURE:
<223> OTHER INFORMATION: CBF1_E_fwdprimer_GCtype2

<400> SEQUENCE: 65
ggcgccggcg cgcccgaaca gagcgaaggt gcgtt      35

<210> SEQ ID NO 66
<211> LENGTH: 30
<212> TYPE: DNA
<213> ORGANISM: Artificial Sequence
<220> FEATURE:
<223> OTHER INFORMATION: CBF1_F_revprimer_LexAMNF

<400> SEQUENCE: 66
actaagctta agacggcggc ggtaaaagca      30

<210> SEQ ID NO 67
<211> LENGTH: 36
<212> TYPE: DNA
<213> ORGANISM: Artificial Sequence
<220> FEATURE:
<223> OTHER INFORMATION: CBF1_G_fwdprimer_GClinkertype2

<400> SEQUENCE: 67
ggcgccggcg cgcccagcga aggtgcgttt tatatg      36

<210> SEQ ID NO 68
<211> LENGTH: 39
<212> TYPE: DNA
<213> ORGANISM: Artificial Sequence
<220> FEATURE:
<223> OTHER INFORMATION: CBF3_I_fwdprimer_GClinkertype2

<400> SEQUENCE: 68
ggcgccggcg cgcccggctt cgacatggag gagacgttg      39

<210> SEQ ID NO 69
<211> LENGTH: 36

<212> TYPE: DNA
<213> ORGANISM: Artificial Sequence
<220> FEATURE:
<223> OTHER INFORMATION: CBF3_I_revprimer_LexAMNF

<400> SEQUENCE: 69
aacaagcttc attaataact ccataacgat acgtcg                                    36

<210> SEQ ID NO 70
<211> LENGTH: 20
<212> TYPE: DNA
<213> ORGANISM: Artificial Sequence
<220> FEATURE:
<223> OTHER INFORMATION: revprimer_fragment1_LexAFL

<400> SEQUENCE: 70
ttcatcggca gccacacgac                                                      20

<210> SEQ ID NO 71
<211> LENGTH: 20
<212> TYPE: DNA
<213> ORGANISM: Artificial Sequence
<220> FEATURE:
<223> OTHER INFORMATION: Fwdprimer_Fragemnt2_LexAFL

<400> SEQUENCE: 71
cgtgtggctg ccgatgaacc                                                      20

<210> SEQ ID NO 72
<211> LENGTH: 23
<212> TYPE: DNA
<213> ORGANISM: Artificial Sequence
<220> FEATURE:
<223> OTHER INFORMATION: revprimer_fragemnt2_LexAFL

<400> SEQUENCE: 72
gccgatgtct ttcatcgcca tcc                                                  23

<210> SEQ ID NO 73
<211> LENGTH: 22
<212> TYPE: DNA
<213> ORGANISM: Artificial Sequence
<220> FEATURE:
<223> OTHER INFORMATION: fwdprimer_fragment3_LexAFL

<400> SEQUENCE: 73
ggatggcgat gaaagacatc gg                                                   22

<210> SEQ ID NO 74
<211> LENGTH: 37
<212> TYPE: DNA
<213> ORGANISM: Artificial Sequence
<220> FEATURE:
<223> OTHER INFORMATION: revprimer_fragment3_LexAFL

<400> SEQUENCE: 74
gggcgcgccg gcgcccagcc agtcgccgtt gcgaata                                   37

<210> SEQ ID NO 75
<211> LENGTH: 219
<212> TYPE: DNA
<213> ORGANISM: Artificial Sequence
<220> FEATURE:
<223> OTHER INFORMATION: fragmentt 1 of LexAFL

<400> SEQUENCE: 75

```
atgaaagcgt taacggccag gcaacaagag gtgtttgatc tcatccgtga tcacatcagc    60
cagacaggta tgccgccgac gcgtgcggaa atcgcgcagc gtttggggtt ccgttcccca   120
aacgcggctg aagaacatct gaaggcgctg gcacgcaaag gcgttattga aattgtttcc   180
ggcgcatcac gcgggattcg tctgttgcag aaagaggaa                          219
```

<210> SEQ ID NO 76
<211> LENGTH: 145
<212> TYPE: DNA
<213> ORGANISM: Artificial Sequence
<220> FEATURE:
<223> OTHER INFORMATION: fragment2 of LexAFL

<400> SEQUENCE: 76

```
ctgttgcaga aagaggaaga agggttgccg ctggtaggtc gtgtggctgc cgatgaacca    60
cttctggcgc aacagcatat tgaaggtcat tatcaggtcg atccttccaa gaaacgcaag   120
ccgaatgctg atttcctgct gcgcg                                         145
```

<210> SEQ ID NO 77
<211> LENGTH: 306
<212> TYPE: DNA
<213> ORGANISM: Artificial Sequence
<220> FEATURE:
<223> OTHER INFORMATION: fragemnt 3 of LexAFL

<400> SEQUENCE: 77

```
tccaagaaac gcaagccgaa tgctgatttc ctgctgcgcg tcagcgggat ggcgatgaaa    60
gacatcggca ttatggatgg tgacttgctg gcagtgcata aaactcagga tgtacgtaac   120
ggtcaggtcg ttgtcgcacg tattgatgac gaagttaccg ttaagcgcct gaaaaaacag   180
ggcaataaag tcgaactgtt gccagaaaat agcgagttta aaccaattgt cgttgacctt   240
cgtcagcaga gcttcaccat tgaagggctg gcggttgggg ttattcgcaa cggcgactgg   300
ctgtaa                                                              306
```

<210> SEQ ID NO 78
<211> LENGTH: 219
<212> TYPE: DNA
<213> ORGANISM: Artificial Sequence
<220> FEATURE:
<223> OTHER INFORMATION: fragment 4 of LexAFLNLS

<400> SEQUENCE: 78

```
atgaaagcgt taacggccag gcaacaagag gtgtttgatc tcatccgtga tcacatcagc    60
cagacaggta tgccgccgac gcgtgcggaa atcgcgcagc gtttggggtt ccgttcccca   120
aacgcggctg aagaacatct gaaggcgctg gcacgcaaag gcgttattga aattgtttcc   180
ggcgcatcac gcgggattcg tctgttgcag aaagaggaa                          219
```

<210> SEQ ID NO 79
<211> LENGTH: 127
<212> TYPE: DNA
<213> ORGANISM: Artificial Sequence
<220> FEATURE:
<223> OTHER INFORMATION: fragment5 of LexAFLNLS

<400> SEQUENCE: 79

```
ctgttgcaga aagaggaaga agggttgccg ctggtaggtc gtgtggctgc cgatgaacca    60
cttctggcgc aacagcatat tgaaggtcat tatcaggtcg atccttccaa gaaacgcaag   120
ccgaatg                                                             127
```

<210> SEQ ID NO 80
<211> LENGTH: 303
<212> TYPE: DNA
<213> ORGANISM: Artificial Sequence
<220> FEATURE:
<223> OTHER INFORMATION: fragment6 of LexAFLNLS

<400> SEQUENCE: 80
tccaagaaac gcaagccgaa tgctgatttc ctgctgcgcg tcagcgggat ggcgatgaaa       60
gacatcggca ttatggatgg tgacttgctg gcagtgcata aaactcagga tgtacgtaac      120
ggtcaggtcg ttgtcgcacg tattgatgac gaagttaccg ttaagcgcct gaaaaaacag      180
ggcaataaag tcgaactgtt gccagaaaat agcgagttta accaattgt cgttgacctt       240 cgtcagcaga gcttcaccat tgaagggctg gcggttgggg ttattcgcaa cggcgactgg      300
ctg                                                                    303

<210> SEQ ID NO 81
<211> LENGTH: 30
<212> TYPE: DNA
<213> ORGANISM: Artificial Sequence
<220> FEATURE:
<223> OTHER INFORMATION: fwdprimer_frag4

<400> SEQUENCE: 81
agactcgaga tgaaagcgtt aacggccagg                                        30

<210> SEQ ID NO 82
<211> LENGTH: 21
<212> TYPE: DNA
<213> ORGANISM: Artificial Sequence
<220> FEATURE:
<223> OTHER INFORMATION: revprimer_frag4

<400> SEQUENCE: 82 ttcctcttc tgcaacagac g                                                  21

<210> SEQ ID NO 83
<211> LENGTH: 20
<212> TYPE: DNA
<213> ORGANISM: Artificial Sequence
<220> FEATURE:
<223> OTHER INFORMATION: fwdprimer_frag5

<400> SEQUENCE: 83
ctgttgcaga aagaggaaga                                                   20

<210> SEQ ID NO 84
<211> LENGTH: 33
<212> TYPE: DNA
<213> ORGANISM: Artificial Sequence
<220> FEATURE:
<223> OTHER INFORMATION: revprimer_frag5

<400> SEQUENCE: 84
cttgcgtttc ttggaaggat cgacctgata atg                                    33

<210> SEQ ID NO 85
<211> LENGTH: 37
<212> TYPE: DNA
<213> ORGANISM: Artificial Sequence
<220> FEATURE:
<223> OTHER INFORMATION: fwdprimer_frag6

<400> SEQUENCE: 85
tccaagaaac gcaagccgaa tgctgatttc ctgctgc 37

<210> SEQ ID NO 86
<211> LENGTH: 37
<212> TYPE: DNA
<213> ORGANISM: Artificial Sequence
<220> FEATURE:
<223> OTHER INFORMATION: revprimer_frag6

<400> SEQUENCE: 86
gggcgcgccg gcgcccagcc agtcgccgtt gcgaata 37

<210> SEQ ID NO 87
<211> LENGTH: 33
<212> TYPE: DNA
<213> ORGANISM: Artificial Sequence
<220> FEATURE:
<223> OTHER INFORMATION: Ampliprom F

<400> SEQUENCE: 87
caggatccac tagtacaatc ccactatcct tcg 33

<210> SEQ ID NO 88
<211> LENGTH: 29
<212> TYPE: DNA
<213> ORGANISM: Artificial Sequence
<220> FEATURE:
<223> OTHER INFORMATION: Ampliprom R

<400> SEQUENCE: 88
tttctagacc atggtgtaat tgtaaatag 29

<210> SEQ ID NO 89
<211> LENGTH: 35
<212> TYPE: DNA
<213> ORGANISM: Artificial Sequence
<220> FEATURE:
<223> OTHER INFORMATION: LexA DBD rev primer

<400> SEQUENCE: 89
gggcccgggc gcgcctggtt caccggcagc cacac 35

<210> SEQ ID NO 90
<211> LENGTH: 98
<212> TYPE: PRT
<213> ORGANISM: Artificial Sequence
<220> FEATURE:
<223> OTHER INFORMATION: CBF1 fragment A

<400> SEQUENCE: 90

Thr Cys Ala Lys Asp Ile Gln Lys Ala Ala Ala Glu Ala Ala Leu Ala
1               5                   10                  15

Phe Gln Asp Glu Thr Cys Asp Thr Thr Thr Thr Asn His Gly Leu Asp
            20                  25                  30

Met Glu Glu Thr Met Val Glu Ala Ile Tyr Thr Pro Glu Gln Ser Glu
        35                  40                  45

Gly Ala Phe Tyr Met Asp Glu Glu Thr Met Phe Gly Met Pro Thr Leu
    50                  55                  60

Leu Asp Asn Met Ala Glu Gly Met Leu Leu Pro Pro Pro Ser Val Gln
65                  70                  75                  80

Trp Asn His Asn Tyr Asp Gly Glu Gly Asp Gly Asp Val Ser Leu Trp
                85                  90                  95

Ser Tyr

<210> SEQ ID NO 91
<211> LENGTH: 86
<212> TYPE: PRT
<213> ORGANISM: Artificial Sequence
<220> FEATURE:
<223> OTHER INFORMATION: CBF1 fragment B

<400> SEQUENCE: 91

Thr Cys Ala Lys Asp Ile Gln Lys Ala Ala Glu Ala Ala Leu Ala
1               5                   10                  15

Phe Gln Asp Glu Thr Cys Asp Thr Thr Thr Thr Asn His Gly Leu Asp
            20                  25                  30

Met Glu Glu Thr Met Val Glu Ala Ile Tyr Thr Pro Glu Gln Ser Glu
        35                  40                  45

Gly Ala Phe Tyr Met Asp Glu Glu Thr Met Phe Gly Met Pro Thr Leu
    50                  55                  60

Leu Asp Asn Met Ala Glu Gly Met Leu Leu Pro Pro Ser Val Gln
65                  70                  75                  80

Trp Asn His Asn Tyr Asp
                85

<210> SEQ ID NO 92
<211> LENGTH: 74
<212> TYPE: PRT
<213> ORGANISM: Artificial Sequence
<220> FEATURE:
<223> OTHER INFORMATION: CBF1 fragment C

<400> SEQUENCE: 92

Thr Cys Ala Lys Asp Ile Gln Lys Ala Ala Glu Ala Ala Leu Ala
1               5                   10                  15

Phe Gln Asp Glu Thr Cys Asp Thr Thr Thr Thr Asn His Gly Leu Asp
            20                  25                  30

Met Glu Glu Thr Met Val Glu Ala Ile Tyr Thr Pro Glu Gln Ser Glu
        35                  40                  45

Gly Ala Phe Tyr Met Asp Glu Glu Thr Met Phe Gly Met Pro Thr Leu
    50                  55                  60

Leu Asp Asn Met Ala Glu Gly Met Leu Leu
65                  70

<210> SEQ ID NO 93
<211> LENGTH: 62
<212> TYPE: PRT
<213> ORGANISM: Artificial Sequence
<220> FEATURE:
<223> OTHER INFORMATION: CBF1 fragment D

<400> SEQUENCE: 93

Thr Cys Ala Lys Asp Ile Gln Lys Ala Ala Glu Ala Ala Leu Ala
1               5                   10                  15

Phe Gln Asp Glu Thr Cys Asp Thr Thr Thr Thr Asn His Gly Leu Asp
            20                  25                  30

Met Glu Glu Thr Met Val Glu Ala Ile Tyr Thr Pro Glu Gln Ser Glu
        35                  40                  45

Gly Ala Phe Tyr Met Asp Glu Glu Thr Met Phe Gly Met Pro
    50                  55                  60

```
<210> SEQ ID NO 94
<211> LENGTH: 43
<212> TYPE: PRT
<213> ORGANISM: Artificial Sequence
<220> FEATURE:
<223> OTHER INFORMATION: CBF1 fragment E

<400> SEQUENCE: 94

Pro Glu Gln Ser Glu Gly Ala Phe Tyr Met Asp Glu Thr Met Phe
1               5                   10                  15

Gly Met Pro Thr Leu Leu Asp Asn Met Ala Glu Gly Met Leu Leu Pro
            20                  25                  30

Pro Pro Ser Val Gln Trp Asn His Asn Tyr Asp
        35                  40

<210> SEQ ID NO 95
<211> LENGTH: 35
<212> TYPE: PRT
<213> ORGANISM: Artificial Sequence
<220> FEATURE:
<223> OTHER INFORMATION: CBF1 fragment F

<400> SEQUENCE: 95

Pro Glu Gln Ser Glu Gly Ala Phe Tyr Met Asp Glu Thr Met Phe
1               5                   10                  15

Gly Met Pro Thr Leu Leu Asp Asn Met Ala Glu Gly Met Leu Leu Pro
            20                  25                  30

Pro Pro Ser
        35

<210> SEQ ID NO 96
<211> LENGTH: 52
<212> TYPE: PRT
<213> ORGANISM: Artificial Sequence
<220> FEATURE:
<223> OTHER INFORMATION: CBF1 fragment G

<400> SEQUENCE: 96

Ser Glu Gly Ala Phe Tyr Met Asp Glu Thr Met Phe Gly Met Pro
1               5                   10                  15

Thr Leu Leu Asp Asn Met Ala Glu Gly Met Leu Leu Pro Pro Pro Ser
            20                  25                  30

Val Gln Trp Asn His Asn Tyr Asp Gly Glu Gly Asp Gly Asp Val Ser
            35                  40                  45

Leu Trp Ser Tyr
    50

<210> SEQ ID NO 97
<211> LENGTH: 70
<212> TYPE: PRT
<213> ORGANISM: Artificial Sequence
<220> FEATURE:
<223> OTHER INFORMATION: CBF1 fragment I

<400> SEQUENCE: 97

Gly Phe Asp Met Glu Glu Thr Leu Val Glu Ala Ile Tyr Thr Ala Glu
1               5                   10                  15

Gln Ser Glu Asn Ala Phe Tyr Met His Asp Gly Ala Met Phe Glu Met
            20                  25                  30

Pro Ser Leu Leu Ala Asn Met Ala Glu Gly Met Leu Leu Pro Leu Pro
        35                  40                  45

Ser Val Gln Trp Asn His Asn His Glu Val Asp Gly Asp Asp Asp Asp
```

```
                50                  55                  60
Val Ser Leu Trp Ser Tyr
65                  70

<210> SEQ ID NO 98
<211> LENGTH: 16
<212> TYPE: DNA
<213> ORGANISM: Artificial Sequence
<220> FEATURE:
<223> OTHER INFORMATION: LexA consensus binding sequence
<220> FEATURE:
<221> NAME/KEY: misc_feature
<222> LOCATION: (5)..(12)
<223> OTHER INFORMATION: n is a, c, g, or t

<400> SEQUENCE: 98
ctgtnnnnnn nnacag                                                   16

<210> SEQ ID NO 99
<211> LENGTH: 12
<212> TYPE: DNA
<213> ORGANISM: Artificial Sequence
<220> FEATURE:
<223> OTHER INFORMATION: LexA consensus in gram postive bacteria
<220> FEATURE:
<221> NAME/KEY: misc_feature
<222> LOCATION: (5)..(8)
<223> OTHER INFORMATION: n is a, c, g, or t

<400> SEQUENCE: 99
gaacnnnngt tc                                                       12

<210> SEQ ID NO 100
<211> LENGTH: 4
<212> TYPE: PRT
<213> ORGANISM: Artificial Sequence
<220> FEATURE:
<223> OTHER INFORMATION: nuclear localization signal

<400> SEQUENCE: 100

Lys Lys Arg Lys
1
```

CONTROLLING GENE EXPRESSION IN PLANTS USING FUSION PROTEIN CONTAINING LEXA BINDING DOMAIN AND DREB TRANSACTIVATION DOMAIN

CROSS REFERENCE TO RELATED APPLICATIONS

This application is a US National Stage Entry under 35 U.S.C. § 371 of International Patent Application No. PCT/US13/55791, filed on Aug. 20, 2013, which claims the benefit of India Provisional Patent Application No. 2583/DELNP/2012, filed Aug. 21, 2012, and U.S. Provisional Application No. 61/715,479, filed Oct. 18, 2012, the entire content of which is herein incorporated by reference.

FIELD OF INVENTION

The present invention relates to compositions and methods useful for regulation of gene expression in plants through a transactivation system using a chimeric transactivator.

BACKGROUND

Recent advances in plant genetic engineering have opened new doors to engineer plants to have improved characteristics or traits. These transgenic plants characteristically have recombinant DNA constructs in their genome that have a protein-coding region operably linked to at least one regulatory region, e.g., a promoter. Novel strategies need to be developed for transgene expression that provide for precise spatiotemporal control. Conventional approaches to the regulation of plant transgene expression by the fusing of a highly expressed promoter element directly with the protein-coding sequence have proved insufficient to meet the stringent safety and technical demands of plant biotechnology today. Commercially the exploitation of plants by transgenic modification is hampered by the inability to introduce and coordinately regulate multiple transgenes in transgenic crops. One conventional approach involves fusing each biosynthetic protein-coding sequence to a common promoter element, followed by repeated transformation into a transgenic plant. This approach is time-consuming, limits further alterations of transgene expression and rather than enabling coordinate transgene expression can lead to cosuppression of transgenes. Also, multiple copies of the same promoter, directing coordinate regulation of multiple genes, can lead to gene inactivation through repeat-induced gene silencing (Ye and Signer, 1996, *Proc. National Acad. Sci.* 93:10881-10886) or other means of gene silencing. A second limitation is that the pattern of expression conferred by the particular promoter employed is inflexible in that the same promoter-dependent pattern of expression is conferred from generation to generation. For imparting certain traits, it is desirable to have the ability to regulate the trait-conferring transgene expression differently in successive generations. A two component transcription factor/target promoter system could be used to address the above limitations of transgene expression with existing promoters. Many positive transcriptional regulatory factors are modular, consisting of a DNA-binding domain and transactivation domain that interacts with components of the transcriptional machinery assembling at the promoter (Ptashne, M. (1988) Nature. October 20; 335(6192):683-9.). Fusing combinations of these elements, derived from different kingdoms, results in production of diverse hybrid factors having defined DNA-binding specificity and transcriptional activation function (Moore et al. (2006) Plant J. 45:651-683; Weinmann et al (1994) *Plant J* 5(4):559-569; U.S. Pat. No. 7,285,416, U.S. Pat. No. 6,252,136, U.S. Pat. No. 6,576,422)

SUMMARY

One embodiment of this invention is a recombinant DNA construct comprising a promoter functional in a plant cell operably linked to a polynucleotide encoding a fusion protein, wherein the polynucleotide comprises: (a) a first nucleotide sequence encoding a first amino acid sequence having a DNA-binding domain wherein the first amino acid sequence is SEQ ID NO:15, 32, 34, 36 or 38 or a functional fragment of SEQ ID NO:15, 32, 34, 36 or 38; and (b) a second nucleotide sequence encoding a second amino acid sequence having a transactivation domain wherein the second amino acid sequence is SEQ ID NO:11, 13, 90-96 or 97 or a functional fragment of SEQ ID NO:11, 13, 90-96 or 97 wherein the fusion protein capable of activating transcription of a heterologous polynucleotide that is operably linked to a LexA operator. In one embodiment, the promoter functional in a plant cell is a tissue-specific promoter. In one embodiment, the promoter functional in a plant cell is an inducible promoter.

In one embodiment, the fusion protein encoded by this recombinant DNA construct is capable of activating transcription of a heterologous polynucleotide operably linked to a minimal promoter and at least one LexA operator sequence; and further wherein the heterologous polynucleotide encodes a heterologous polypeptide capable of modifying an agronomic characteristic in the plant cell.

In one embodiment, the at least one LexA operator sequence comprises at least one sequence selected from the group consisting of: a recA-type operator sequence and a caa-type operator sequence.

In one embodiment, the recA-type operator sequence comprises the sequence given in SEQ ID NO:22 and the caa-type operator sequence comprises the sequence given in SEQ ID NO:23.

In one embodiment, the transactivator domain is operably linked to a nuclear localization sequence (NLS).

In one embodiment, the NLS comprises the sequence of SEQ ID NO:39.

In another embodiment, this invention concerns a vector, cell, plant, or seed comprising at least one of the recombinant DNA constructs described in the present invention.

One embodiment of the present invention is a method of regulating the expression of a heterologous polynucleotide in a plant, wherein the method comprises the steps of: (a) obtaining a plant comprising a first recombinant DNA construct comprising a promoter functional in a plant cell operably linked to a polynucleotide encoding a fusion protein as described herein, and a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; and (b) growing the plant of step (a) under conditions in which the first recombinant DNA construct is expressed.

One embodiment of the present invention is a method of regulating the expression of a heterologous polynucleotide in a plant, wherein the method comprises the steps of: (a) obtaining a plant comprising a first recombinant DNA construct comprising a promoter functional in a plant cell operably linked to a polynucleotide encoding a fusion protein as described herein; (b) introducing into the plant of step (a) the second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; and (c) growing the plant under conditions in which the first recombinant DNA construct is expressed.

One embodiment of the present invention is a method of regulating the expression of a heterologous polynucleotide in a plant, wherein the method comprises the steps of: (a) introducing into a regenerable plant cell the first recombinant DNA construct comprising a promoter functional in a plant cell operably linked to a polynucleotide encoding a fusion protein as described herein, and a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; and (b) regenerating a transgenic plant from the regenerable plant cell of step (a) wherein the transgenic plant comprises in its genome the first recombinant DNA construct and the second recombinant DNA construct. The plant may be grown under conditions in which the first recombinant DNA construct is expressed. The first and the second recombinant DNA constructs of step (a) may be introduced into the regenerable plant cell sequentially or simultaneously.

One embodiment of the present invention is a method of regulating the expression of a heterologous polynucleotide in a plant, wherein the method comprises the steps of: (a) introducing into a regenerable plant cell the first recombinant DNA construct comprising a promoter functional in a plant cell operably linked to a polynucleotide encoding a fusion protein as described herein, and a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; (b) regenerating a transgenic plant from the regenerable plant cell of step (a) wherein the transgenic plant comprises in its genome the first recombinant DNA construct and the second recombinant DNA construct; and (c) obtaining a progeny plant derived from the transgenic plant of step (b), wherein the progeny plant comprises in its genome the first recombinant DNA construct and the second recombinant DNA constructs described herein; and (d) growing the progeny plant under conditions in which the first recombinant DNA construct is expressed. The first and the second recombinant DNA constructs of step (a) may be introduced into the regenerable plant cell sequentially or simultaneously.

In one embodiment, the invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the recombinant constructs described in the present invention is selected from the group consisting of: *Arabidopsis*, maize, soybean, sunflower, sorghum, canola, mustard, wheat, alfalfa, cotton, rice, barley, millet, sugar cane and switchgrass.

BRIEF DESCRIPTION OF DRAWINGS AND SEQUENCE LISTING

Figure 1:
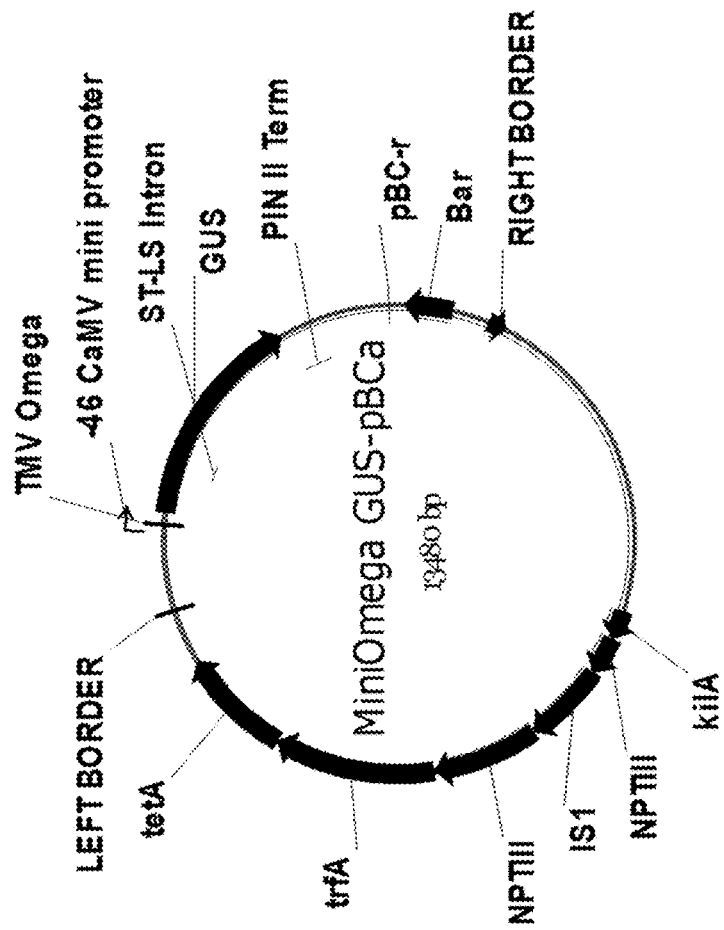
FIG. 1 shows a map of the MiniOmega_GUS-pBC construct.

The Sequence Descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

SEQ ID NOS:1 and 2 are the forward and reverse primers, respectively, for amplifying the full-length LexA gene.

SEQ ID NOS:3 and 4 are the forward and reverse primers, respectively, for amplifying the LexA ORF.

SEQ ID NOS:5 and 6 are the forward and reverse primers, respectively, for amplifying the AtCBF1 ORF.

SEQ ID NOS:7 and 8 are the forward and reverse primers, respectively, for amplifying the AtCBF3 ORF.

SEQ ID NO:9 is the sequence of the *Arabidopsis thaliana* CBF1 cDNA.

SEQ ID NO:10 is the nucleotide sequence of the *Arabidopsis thaliana* CBF1 ORF.

SEQ ID NO:11 is the amino acid sequence of the *Arabidopsis thaliana* CBF1, encoded by SEQ ID NO:10.

SEQ ID NO:12 is the nucleotide sequence of the *Arabidopsis thaliana* CBF3 ORF.

SEQ ID NO:13 is the amino acid sequence of the *Arabidopsis thaliana* CBF3, encoded by SEQ ID NO:12.

SEQ ID NO:14 is the nucleotide sequence of the LexA ORF.

SEQ ID NO:15 is the amino acid sequence of the LexA protein, encoded by SEQ ID NO:14.

SEQ ID NO:16 is the sequence of the CaMV 35S promoter minimal sequence.

SEQ ID NO:17 is the TMV omega sequence.

SEQ ID NO:18 is the sequence of the Minicorepromoter upper oligo.

SEQ ID NO:19 is the sequence of the Minicorepromoter lower oligo.

SEQ ID NO:20 is the LexA full-length sequence.

SEQ ID NO:21 is the CaMV 35S promoter-TMV omega sequence.

SEQ ID NO:22 is the sequence of a recA operator.

SEQ ID NO:23 is the sequence of a caa operator.

SEQ ID NO:24 is the sequence of a hybrid operator comprising 2 copies of a recA operator (SEQ ID NO:22) operably linked to 2 copies of a caa operator (SEQ ID NO:23).

SEQ ID NO:25 and SEQ ID NO:26 are the sequences of the oligonucleotides used for recA operator multimerization.

SEQ ID NO:27 and SEQ ID NO:28 are the sequences of the oligonucleotides used for caa operator multimerization.

SEQ ID NO:29 and SEQ ID NO:30 are the sequences of the oligonucleotides used for hybrid operator synthesis.

SEQ ID NO:31 is the nucleotide sequence of a LexA wt DBD.

SEQ ID NO:32 is the amino acid sequence of the LexA wt DBD, encoded by the sequence given in SEQ ID NO:31.

SEQ ID NO:33 is the nucleotide sequence of the LexAMNF mutant of LexA.

SEQ ID NO:34 is the amino acid sequence of LexAMNF mutant of LexA, encoded by the sequence given in SEQ ID NO:33.

SEQ ID NO:35 is the nucleotide sequence of the LexAFL mutant of LexA.

SEQ ID NO:36 is the amino acid sequence of the LexAFL mutant of LexA, encoded by the sequence given in SEQ ID NO:35.

SEQ ID NO:37 is the nucleotide sequence of the LexAFLNLS mutant of LexA.

SEQ ID NO:38 is the amino acid sequence of the LexAFLNLS mutant of LexA, encoded by the sequence given in SEQ ID NO:37.

SEQ ID NO:39 is the consensus NLS sequence.

SEQ ID NOS:40-46 are the sequences of *Arabidopsis thaliana* CBF1 fragments A-G respectively, as given in Table 3.

SEQ ID NO:47 is the sequence of *Arabidopsis thaliana* CBF3 fragment I, as given in Table 3.

SEQ ID NOS:48-74 and SEQ ID NOS: 81-89 are the sequences of the primers used for amplifying the various LexA and CBF fragments and creating their fusions, as given in the tables 4-7.

SEQ ID NOS:75-80 are the sequences of the different LexAFL and LexAFLNLS fragments used for amplifying LexAFL and LexAFLNLS.

SEQ ID NOS:90-96 are the amino acid sequences of *Arabidopsis thaliana* CBF1 fragments A-G respectively, encoded by the nucleotide sequences given in SEQ ID NOS:40-46.

SEQ ID NO:97 is the amino acid sequence of the *Arabidopsis thaliana* CBF3 fragment I, encoded by the nucleotide sequence given in SEQ ID NO:47.

SEQ ID NO:98 is the LexA binding consensus sequence in Gram negative bacteria.

SEQ ID NO:99 is the LexA binding consensus sequence in Gram positive bacteria.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS*. 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Regulatory Sequences:

A recombinant DNA construct (including a suppression DNA construct) of the present invention may comprise at least one regulatory sequence.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to produce a desired phenotype, e.g., to enhance drought tolerance. This effect has been observed in *Arabidopsis* (Kasuga et al. (1999) *Nature Biotechnol.* 17:287-91).

Suitable constitutive promoters for use in a plant host cell include, but are not limited to, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, but are not limited to, for example, those discussed in U.S. Pat. Nos. 5,608,149; 5,608,144; 5,604,121; 5,569,597; 5,466,785; 5,399,680; 5,268,463; 5,608,142; and 6,177,611.

For constitutive expression in plants viral promoters may be utilized in plant expression vectors. These include the 35S RNA and 19S RNA promoters of CaMV (Brisson, et al., *Nature*, 310:511, 1984, Odell, et al., *Nature*, 313:810, 1985); the promoter from Figwort Mosaic Virus (FMV) (Gowda, et al., *J. Cell Biochem.*, 13D:301, 1989) and the coat protein promoter of TMV (Takamatsu, et al., *EMBO J.* 6:307, 1987). Additional promoters include the nopaline synthase promoter (An et al., (1988) *Plant Physiol.* 88:547); and the octopine synthase promoter (Fromm et al., (1989) *Plant Cell* 1: 977).

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include, but are not limited to, soybean Kunitz trypsin inhibitor (Kti3, Jofuku and Goldberg, *Plant Cell* 1:1079-1093 (1989)), patatin (potato tubers) (Rocha-Sosa, M., et al. (1989) *EMBO J.* 8:23-29), convicilin, vicilin, and legumin (pea cotyledons) (Rerie, W. G., et al. (1991) *Mol. Gen. Genet.* 259:149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci. U.S.A.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564), and sporamin (sweet potato tuberous root) (Hattori, T., et al. (1990) *Plant Mol. Biol.* 14:595-604). Promoters of seed-specific genes operably linked to heterologous coding regions in chimeric gene constructions maintain their temporal and spatial expression pattern in transgenic plants. Such examples include, but are not limited to, *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, but are not limited to, for example, promoters regulated by light, heat, stress, flooding or drought, phytohormones, wounding, or chemicals such as ethanol, jasmonate, salicylic acid, or safeners.

Examples of inducible promoters useful in plants include those induced by chemical means, such as the yeast metallothionein promoter which is activated by copper ions (Mett, et al., (1993) *Proc. Natl. Acad. Sci., U.S.A.,* 90:4567); In2-1 and In2-2 regulator sequences which are activated by substituted benzenesulfonamides, e.g., herbicide safeners (Hershey, et al., (1991) *Plant Mol. Biol.,* 17:679): and the GRE regulatory sequences which are induced by glucocorticoids (Schena, et al. (1991), *Proc. Natl. Acad. Sci., U.S.A.,* 88:10421). Plant promoters also include the light-inducible promoter from the small subunit of ribulose bis-phosphate carboxylase (ssRUBISCO) (Coruzzi, et al., (1984) *EMBO J.,* 3:1671; Broglie, et al., (1984) *Science,* 224:838), promoters regulated by heat (Callis et al., (1988) *Plant Physiol.* 88:965; Ainley, et al. (1993) *Plant Mol. Biol.* 22: 13-23; hormones, such as abscisic acid (Marcotte et al., (1989) *Plant Cell* 1: 969); wounding (e.g., wun1, Siebertz et al., (1989) *Plant Cell* 1: 961; and chemicals such as methyl jasminate or salicylic acid (Gatz et al., (1997) *Ann. Rev. Plant Physiol. Plant Mol. Biol.* 48: 89-108).

Tissue specific promoters may also be utilized for expression of genes in plants. Examples of tissue specific promoters useful in transgenic plants include, but are not limited to the cdc2a promoter and cyc07 promoter (Ito, et al., (1994) *Plant Mol. Biol.,* 24:863; Martinez, et al. (1992) *Proc. Natl. Acad. Sci. USA,* 89:7360; Medford, et al., (1991) *Plant Cell,* 3:359; Terada, et al. (1993) *Plant Journal,* 3:241; Wissenbach, et al., (1993) *Plant Journal,* 4:411). Additional examples of tissue specific promoters that are utilized in plants include, but are not limited to, the histone promoter (Atanassova, et al., (1992) *Plant Journal,* 2:291); the cinnamyl alcohol dehydrogenase (CAD) promoter (Feuillet, et al., (1995) *Plant Mol. Biol.,* 27:651); the mustard CHS1 promoter (Kaiser, et al., (1995) *Plant Mol. Biol.,* 28:231); the bean grp 1.8 promoter (Keller, et al., (1994) *Plant Mol. Biol.,* 26:747); the PAL1 promoter (Ohl, et al. (1990) *Plant Cell,* 2:837); and the chalcone synthase A promoter (*Plant Mol. Biol.,* (1990)15:95-109). In addition, the timing of the expression can be controlled by using promoters such as those acting at senescence (Gan and Amasino (1995) *Science* 270: 1986-1988); or late seed development (Odell et al. (1994) *Plant Physiol.* 106:447-458).

Examples of other promoters include, but are not limited to, root-specific promoters such as root-specific promoters disclosed in U.S. Pat. Nos. 5,618,988, 5,837,848 and 5,905, 186 or the prxEa promoter in Wanapu and Shinmyo (1996) *Ann. N.Y. Acad. Sci.* 782:107-113 or Miao et al. (1991) *Plant Cell* 3:11-22 or Hirel et al. (1992) *Plant Mol. Biol.* 20:207-218), seed-specific promoters such as the napin, phaseolin or DC3 promoter described in U.S. Pat. No. 5,773,697, the oleate 12-hydroxylase: desaturase promoter from *Lesquerella* (Broun et al (1998) *Plant J.* 13:201-210), the oleosin promoter or *Arabidopsis* (Plant et al (1994) *Plant Mol. Biol.* 25:193-205), a zein promoter of maize (Russel et al (1997) *Transgenic Res.* 6:157-168), the glutelin promoters of rice (Washida et al. *Plant Mol Biol.* (1999) 40:1-12) and maize (Thomas et al (1990) *Plant Cell* 2:1171-1180), fruit specific promoters such as those active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol. Biol.* 11:651), pollen-active promoters such as PTA29, PTA26 and PTA13 (U.S. Pat. No. 5,792,929), promoters active in vascular tissue (Ringli and Keller (1998) *Plant Mol. Biol.* 37:977-988), flower-specific (Kaiser et al, (1995) *Plant Mol. Biol.* 28:231-243), pollen (Baerson et al. (1994) *Plant Mol. Biol.* 26:1947-1959), carpels (Ohl et al. (1990) *Plant Cell* 2:837-848), pollen and ovules (Baerson et al. (1993) *Plant Mol. Biol.* 22:255-267).

Examples of preferred inducible or tissue-specific promoters include, but are not limited to, Rd 29a (Yamaguchi-Shinozaki and Shinozaki (1993) *Plant Physiol. March;* 101:1119-20), LTP1 (Thoma et al. (1994) *Plant Physiol,* 105(1):35-45), STM (Long et al. (1996) *Nature.* 1996 379: 66-9), rbcS (Krebbers (1988) *Plant Mol Biol.* 11: 745-759), sucrose synthase (Martin et al. (1993) *Plant J.* 4:367-77), EIR1 (Luschnig et al. (1998) *Genes Dev.* 12:2175-87), IL (Bernhard, and Matile, GenBank Accession Number M83534), PR1 (Lebel et al. (1998) *Plant J.* 16:223-33), AGL1 (Ma et al. (1991) *Genes* 5:484-95), AP1 (Mandel et al. (1992) 360:273-7), E4 (Cordes et al. (1989) *Plant Cell.* 1(10):1025-34), or GL2 (Rerie et al. (1994) *Genes Dev.* 8(12):1388-99).

Plant RNA polymerase II promoters, like those of other higher eukaryotes, are comprised of several distinct "cis-acting transcriptional regulatory elements," or simply "cis-elements," each of which appears to confer a different aspect of the overall control of gene expression. Examples of such cis-acting elements include, but are not limited to, such as TATA box and CCAAT or AGGA box. The promoter can roughly be divided in two parts: a proximal part, referred to as the core, and a distal part. The proximal part is believed to be responsible for correctly assembling the RNA polymerase II complex at the right position and for directing a basal level of transcription, and is also referred to as "minimal promoter" or "basal promoter". The distal part of the promoter is believed to contain those elements that regulate the spatio-temporal expression. In addition to the proximal and distal parts, other regulatory regions have also been described, that contain enhancer and/or repressors elements The latter elements can be found from a few kilobase pairs upstream from the transcription start site, in the introns, or even at the 3' side of the genes they regulate (Rombauts, S. et al. (2003) *Plant Physiology* 132:1162-1176, Nikolov and Burley, (1997) *Proc Natl Acad Sci USA* 94: 15-22), Tjian and Maniatis (1994) *Cell* 77: 5-8; Fessele et al., 2002 *Trends Genet* 18: 60-63, Messing et al., (1983) *Genetic Engineering of Plants: an Agricultural Perspective,* Plenum Press, NY, pp 211-227).

Enhancer sequences refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

Recombinant DNA constructs of the present invention may also include other regulatory sequences, including but not limited to, translation leader sequences, introns, and polyadenylation recognition sequences.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

Many genes exhibit enhanced expression on inclusion of an intron in the transcribed region, especially when the intron is present within the first 1 kb of the transcription start site. The increase in gene expression by presence of an intron can be at both the mRNA (transcript abundance) and protein levels. The mechanism of this Intron Mediated Enhancement (IME) in plants is not very well known (Rose et al., *Plant Cell,* 20: 543-551 (2008) Le-Hir et al, *Trends Biochem Sci.* 28: 215-220 (2003), Buchman and Berg, *Mol. Cell Biol.* (1988) 8:4395-4405; Callis et al., *Genes Dev.* 1(1987):1183-1200).

An "enhancing intron" is an intronic sequence present within the transcribed region of a gene which is capable of enhancing expression of the gene when compared to an intronless version of an otherwise identical gene. An enhancing intronic sequence might also be able to act as an enhancer when located outside the transcribed region of a gene, and can act as a regulator of gene expression independent of position or orientation (Chan et. al. (1999) *Proc. Natl. Acad. Sci.* 96: 4627-4632; Flodby et al. (2007) *Biochem. Biophys. Res. Commun.* 356: 26-31).

Eukaryotic transcriptional activators are modular proteins that are typically composed of a sequence-specific DNA binding domain and an activating region (or domain). Activators interact through their activating regions with components of the RNA polymerase II transcriptional apparatus that bind promoters. It has been shown that some activators can also interact with factors that modify or remodel nucleosomes (chromatin). According to their amino acid constitution, activation domains have been classified as acidic (e.g. the viral VP16 and the yeast Gal4), glutamine-rich (e.g. SP1) or proline-rich (e.g. CTF).

Binding of the activator to DNA serves merely to locate it to a position from which the activation domain can activate transcription. DNA binding per se is clearly not sufficient for activating transcription. Many genes, especially in higher eukaryotes, are activated not by just one but by several activators that act in concert. The use of several, and often different, activators to activate one gene establishes a combinatorial control that allows differential regulation of many genes with a relatively small number of transcriptional activators.

"Transactivation" refers herein to the activation of the expression of a heterologous polynucleotide (effector locus) by the introduction of a "transcriptional activator" (activating locus or driver locus).

The "transcriptional activator" referred to herein may be a chimeric transcriptional activator, comprising DNA-binding domain and transactivation domains from different proteins. The "DNA-binding domain" referred to herein may be the DNA-binding domain from a LexA protein. The transactivator domain may be a CBF1 or CBF3 "transactivator domain".

The "transactivation system" described herein comprises generation of two different loci. The first locus comprises the "activator locus" or the "driver locus" and the second locus comprises the "effector locus".

In the invention disclosed here, the "activator locus" comprises a promoter functional in a plant cell, operably linked to a chimeric transcriptional activator comprising a LexA DNA-binding domain and a transactivator domain, e.g., the activation domain of a CBF protein, wherein the LexA DNA-binding domain and the activation domain are operably linked to each other. In one embodiment, the chimeric transactivator may comprise the LexA N-terminal DNA binding domain. In one embodiment the chimeric transactivator may comprise residues 1-87 of the LexA polypeptide. In one embodiment the chimeric transactivator may comprise the full length LexA polypeptide.

The terms "chimeric transcriptional activator" "fusion protein" or "chimeric protein" are used interchangeably herein and refer to a fusion protein comprising the DNA-binding domain of a LexA repressor protein and a transactivation domain, e.g., the activator domain of the C-repeat binding factor (CBF) protein. The chimeric transactivator protein may comprise the DNA-binding domain (DBD) or the full length LexA protein. The fusion protein comprises a first nucleotide sequence encoding a first amino acid sequence having a DNA binding domain wherein the first amino acid sequence is SEQ ID NO:15, 32, 34, 36 or 38 or a functional fragment of SEQ ID NO:15, 32, 34, 36 or 38; and a second nucleotide sequence encoding a second amino acid sequence encoding a second amino acid sequence having a transactivation domain wherein the second amino acid sequence is SEQ ID NO:11, 13, 90-96 or 97 or a functional fragment of SEQ ID NO:11, 13, 90-96 or 97.

The "effector locus" comprises a second recombinant construct comprised of at least one LexA binding site (operator sequence) operably linked to a minimal promoter and a heterologous polynucleotide.

The expression of the heterologous polynucleotide is regulated by the expression of the fusion protein.

The heterologous polynucleotide is operably linked to a minimal promoter. A minimal promoter contains only the proximal promoter elements for binding of the basal transcription apparatus but lacks binding sites for endogenous transcription factors. It is therefore transcriptionally inactive allowing the construct to be introduced into plants and maintained without inducing expression of the heterologous polynucleotide. The minimal promoter is used to minimize the background expression in the absence of the transactivator.

Minimal promoters are well known in the art and several are described in U.S. patent application publication numbers 2007/0009487 and 2006/0242717. Examples of minimal promoters include, but are not limited to, CaMV 35S minimal promoter, SV40 minimal promoter, and Hsp70 minimal promoter.

A minimal or basal promoter is a polynucleotide molecule that is capable of recruiting and binding the basal transcription machinery.

The "transactivation system" described herein may comprise generation of two different kinds of plant lines. One is referred to herein as the "activator line", "activator plant line" or the "driver line" and the other line is referred to herein as the "effector line" or "effector plant line". The "activator line" comprises the activator locus and the "effector line" comprises the effector locus comprising the heterologous polynucleotide, the expression of which is regulated by the expression of the chimeric transcriptional activator.

Each of these "driver" (or "activator") and "effector" genes can be separately transformed into the genome of a plant species such that transformants harboring one component are distinct from transformants harboring the second component. The two components can then be combined into the genome of one plant by genetic crossing of the two transformants harboring the two separate components. The expression of the heterologous polynucleotide in the progeny plant which comprises the driver locus as well as the activator locus is regulated by the expression of the chimeric transcriptional activator. The expression of the chimeric transcriptional activator may be regulated by constitutive, tissue-specific or inducible promoter or regulatory elements.

Crossing a driver plant line with an effector plant line generates double transgenic offspring capable of expressing the heterologous polynucleotide regulated by the expression of the chimeric transactivator. In one embodiment of the invention, combinatorial experiments can be done for bringing the driver locus and the effector locus together in the same plant: one driver line can be crossed to different effector lines to express different heterologous polynucleotides with the same expression pattern and regulatory control. Conversely, the same effector line can be crossed to various drivers to express one heterologous polynucleotide in different spatiotemporal manner.

Then specific crosses can be made in a combinatorial manner between individual members from the two pools of plants: a first pool engineered to contain specific regulatory sequences (such as promoters) and a second pool engineered to contain genes of interest. The gene of interest is expressed only under control of each different promoter in the progeny plant, providing the same effect as if each plant had been transformed initially with the specific gene-promoter combination. In this manner large numbers of specific gene-promoter combinations can therefore be made and the effect on transcription expression and trait improvement investigated with minimal time and expense. (Liu et al. U.S. Pat. No. 5,968,793 and Guyer et al. (1998) *Genetics* 149: 633-639).

Trait improvements for any plant may be investigated by this method. The plant may be a crop plant such as maize, soybean, wheat, corn, potato, cotton, rice, oilseed rape (including canola), sunflower, alfalfa, sugarcane and turf; or a fruit or vegetable plant, such as apple, banana, blackberry, blueberry, strawberry, and raspberry, cantaloupe, carrot, cauliflower, coffee, cucumber, eggplant, grape, honeydew, lettuce, mango, melon, onion, papaya, peas, peppers, pineapple, spinach, squash, sweet corn, tobacco, tomato, watermelon, rosaceous fruits (such as peach, cherry and plum) and vegetable brassicas (such as broccoli, cabbage, cauliflower, brussel sprouts and kohlrabi). Other crops, fruits and vegetables whose trait may be improved include barley, sorghum, currant, avocado, citrus fruits such as oranges, lemons, grapefruit and tangerines, artichoke, currant, cherries, nuts such as the walnut and peanut, pear, endive, leek, roots, such as arrowroot, beet, cassava, turnip, radish, yam, sweet potato and beans.

Thus, the "chimeric transcriptional activator" (or "driver") and the "heterologous polynucleotide" can be combined into the genome of a plant cell by transforming a first plant cell with the first construct, transforming a second plant cell with the second construct, growing fertile mature plants from the first and second transformed plant cells and genetically crossing the transformed plants to produce progeny whose genome contains the first and second constructs.

The LexA (locus for X-ray sensitivity A) protein is a regulator of the SOS response to DNA damage in *Escherichia coli*. In *Escherichia coli*, upon sensing DNA-damage, RecA (recombinase A) stimulates cleavage of the LexA repressor, inducing more than 40 genes that comprise the SOS global regulatory network.

The *E. coli* LexA gene encodes a 202 amino acid protein that folds into two structurally defined domains, which are linked by a flexible hinge region. LexA protein is a repressor protein, which, during normal bacterial growth downregulates its own expression and, in *E. coli*, the expression of at least 43 unlinked genes. Intact LexA dimerises by the carboxy-terminal domain (CTD), and binds to DNA sequences via a helix-turn-helix in its amino-terminal domain (NTD). LexA binds as a dimer with varying affinities to single or multiple copies of gene-specific LexA DNA-binding motifs (LexAop) found upstream of its target genes.

The key catalytic residues in LexA are Ser119 and Lys156. The Ser-Lys dyad catalyzes the cleavage of the bond between residues Ala84 and Gly85.

The consensus DNA target for *E. coli* LexA is CTGT-$N_8$-ACAG (SEQ ID NO:98), which consists of a palindrome. This consensus is conserved in many Gram-negative bacteria, whilst in Gram-positive bacteria; the consensus is GAAC-$N_4$-GTTC (SEQ ID NO:99). In *E. coli*, approximately 30 LexA binding sites have been identified, but LexA also appears to interact with at least 19 targets that lack a conventional site. Promoters of different genes of the SOS response pathway in *E. Coli* have different LexA operator sequences, the LexA operator sequence upstream of the recA gene is called the "rec operator" or "recA operator", and that found in the colicin A promoter is called the "caa operator". The binding affinity of LexA towards these sequences is different.

The term "LexA operator (LexAop)" or "LexA DNA-binding motif" as used herein refers to the polynucleotide sequence to which the LexA binds through its DNA-binding domain (DBD).

The terms "rec operator" and "recA operator", used interchangeably herein refer to the LexA operator sequence found within the recA promoter and corresponds to SEQ ID NO:22. One or multiple copies of the recA operator can be operably linked to each other to comprise the target sequence that LexA can bind to.

The term "caa operator" refers to herein as the LexA operator sequence found within the colicin A promoter and corresponds to SEQ ID NO:23. Single or multiple copies of the recA operator can be operably linked to each other to comprise the target sequence that LexA can bind to.

The term "hybrid operator" as used herein refers to a target sequence that LexA can bind to, that is comprised of at least one copy each of at least two non-identical LexA operator sequences. The "hybrid operator" can comprise one copy each of a recA operator (SEQ ID NO:22) and a caa operator (SEQ ID NO: 23). The "hybrid operator" can comprise two copies each of a recA operator (SEQ ID NO:22) and a caa operator (SEQ ID NO:23). The "hybrid operator" can comprise more than two copies each of a recA operator (SEQ ID NO:22) and a caa operator (SEQ ID NO:23).

The chimeric transactivator protein may comprise the DNA-binding domain (DBD) or the full-length LexA protein. The LexA protein may comprise one or more amino acid changes to increase its activity and stability. The LexA polypeptide may have a mutation at residue 85 to change the amino acid Glycine (Gly) to Alanine (G85 to A85). The LexA polypeptide may have a mutation at residue 71 to change the amino acid Glutamine (Glu) to Lysine (E71 to K71). The LexA polypeptide may have a mutation at residue 119 to change the amino acid Serine (Ser) to Alanine (S119 to A119).

An NLS consensus sequence may be operably linked to the chimeric transactivator. In one embodiment, the sequence of the NLS is SEQ ID NO:39

The terms "C-repeat/dehydration responsive element binding factor protein" (CBF) and "dehydration responsive element binding factor" (DREB) are used interchangeably herein. The transactivator domain of a CBF protein refers to the domain that is responsible for activating transcription from a promoter, but by itself cannot bind DNA. Upon fusion with a DNA-binding domain from a transcription factor, the transcription activation domain within the fusion protein is capable of activating transcription.

In one embodiment, the polynucleotide sequence of the transactivation domain of the CBF protein comprises the nucleotide sequence of SEQ ID NOS:11, 13, 90-96 or 97.

The DREB proteins namely, DREB1 and DREB2, involved in two separate signal transduction pathways under low temperature and dehydration, respectively, are important APETALA2 (AP2)/ethylene responsive factor (ERF) plant transcription factors (TFs) that induce a set of abiotic stress-related genes. DREB genes play an important role in the ABA-independent stress-tolerance pathways that induce the expression of various stress-responsive genes in plants. The first isolated cDNAs encoding DRE (C-repeat/dehydration responsive element) binding proteins, CBF1 (CRT binding factor1), DREB1A and DREB2A were first isolated by using yeast one-hybrid screening (Stockinger, E. J et al. (1997) *Proc Natl Acad Sci.* 94:1035-1040; Liu et al., 1998) from *Arabidopsis*. Since then, numerous DREB genes have been isolated from a number of plants. These proteins specifically bind to the DRE sequence and activate the expression of genes driven by it. DREB1B/CBF1/At4 g25490, DREB1A/CBF3/At4 g25480, and DREB1C/CBF2/At4 g25470 genes lie in tandem on chromosome 4 of *Arabidopsis*.

Expression of the *Arabidopsis* DREB1/CBF genes is induced by cold, while the DREB2 genes are induced by dehydration, high-salinity, and heat stresses generally. However, CBF4/DREB1D, DREB1E/DDF2, and DREB1F/DDF1 are induced by osmotic stress, suggesting the existence of cross-talk between the DREB1 and the DREB2 pathways.

The *Arabidopsis* CBF proteins activate expression of a set of genes whose upstream regulatory sequences typically harbor one or more copies of the CRT/DRE (C-repeat/dehydration responsive element), the cis-acting DNA regulatory element controlling low temperature induced expression of the *Arabidopsis* cold-regulated (COR) genes. The NH3-terminal 115 amino acids direct CBF1 to target genes and the COOH-terminal 98 amino acids function in trans-activation.

The CBFs are members of the AP2 domain-containing protein superfamily that has about 145 members in *Arabidopsis* (Riechmann and Meyerowitz, 1998 *Biol Chem.* 379 (6):633-46.) and are distinguished by the presence of the CBF signature sequences (Jaglo, K. R et al., 2001 *Plant Physiol.* 127(3): 910-917). These two motifs flank the AP2 domain and are thought to impart specificity and targeting of CBFs to their cognate cis-acting DNA binding site, the CRT/DRE. The CBFs are not unique to *Arabidopsis*; cDNAs encoding CBF-like proteins have been identified and characterized in numerous species across the plant kingdom (Jaglo et al., 2001; Choi et al., 2002; Gao et al., 2002; Dubouzet et al., 2003; Zhang et al., 2004). The CBFs have been shown to function across species barriers.

Wang et al ((2005) *Plant Mol. Biol.* 58:543-559) have shown that the carboxy-terminal region is remarkably tolerant of amino acid substitutions. They have also shown that the CBF activation region harbors substantial functional redundancy that ensures trans-activation.

As will be evident to one of skill in the art, any nucleic acid of interest can be expressed using the methods of the present invention. Examples of such nucleic acids include, but are not limited to, disease and insect resistance genes, genes conferring nutritional value, genes to confer male and/or female sterility, antifungal, antibacterial or antiviral genes, and the like. Likewise, the method can be used to express any nucleic acid that controls gene expression. Examples of nucleic acids that could be used to control gene expression include, but are not limited to, antisense oligonucleotides, suppression DNA constructs, or nucleic acids encoding transcription factors.

Genes of interest can be genes conferring modified agronomic traits and characteristics including, but not limited to, yield, heterosis, oil content and nutritional value. The modified agronomic trait may be an increase in the trait. General categories of genes of interest include, for example, those genes involved in information, such as Zinc fingers, those involved in communication, such as kinases, and those involved in housekeeping, such as heat-shock proteins. More specific categories of transgenes, for example, include genes encoding important traits for agronomics, insect resistance, disease resistance, herbicide resistance, sterility, grain characteristics and commercial products. The gene of interest may also be a screenable or selectable marker.

Agronomically important traits such as oil, starch and protein content can be genetically altered in addition to using traditional breeding methods. Modifications include increasing or decreasing the content of oleic acid, saturated and unsaturated oils, increasing levels of lysine and sulfur and providing essential amino acids, and also modification of starch. Other proteins include methionine-rich plant proteins such as from sunflower seed (Lilley, et al. *Proceedings of the World Congress on Vegetable Protein Utilization in Human Foods and Animal Feedstuffs*, Applewhite, H. (ed.); American Oil Chemists Soc., Champaign, Ill.; (1989) 497-502; corn (Pedersen, et al. *J. Biol. Chem.* (1986) 261:6279; Kirihara et al. *Gene* (1988) 71:359; and rice (Musumura, et al. *Plant Mol. Biol.* (1989) 12:123. These references are herein incorporated by reference.

In addition to the various regulatory elements, the recombinant constructs can also contain a selectable or a screenable marker, or both. The nucleic acid sequence serving as the selectable or a screenable marker functions to produce a phenotype in cells that facilitates their identification relative to cells not containing the marker. Useful selectable and screenable markers include, but are not limited to, GUS, green fluorescent protein (GFP), luciferase (LUX), antibiotic resistance sequences, and herbicide tolerance sequences.

Selectable marker genes may be utilized for the selection of transformed cells or tissues. Examples of selectable marker genes include, but are not limited to, genes encoding antibiotic resistance, such as nptII which encodes neomycin phosphotransferase II (NEO), hpt which encodes hygromycin phosphotransferase (HPT), and the monocot-optimized cyanamide hydratase gene (moCAH) (see U.S. Pat. No. 6,096,947) as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480483; Gossen (1993) Ph.D. Thesis, University of Heidelberg; Reines et al. (1993) *Proc. Natl.*

*Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:46474653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Where appropriate, the gene sequence(s) may be modified to optimize for increased expression in the transformed plant. Examples of such modifications include, but are not limited to, synthesizing the genes using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391 and Murray et al. (1989) *Nucleic Acids Res.* 17:477-498.

EMBODIMENTS

One embodiment of this invention is a recombinant DNA construct comprising a promoter functional in a plant cell operably linked to a polynucleotide encoding a fusion protein, wherein the polynucleotide comprises: (a) a first nucleotide sequence encoding a first amino acid sequence having a DNA-binding domain wherein the first amino acid sequence is SEQ ID NO:15, 32, 34, 36 or 38 or a functional fragment of SEQ ID NO:15, 32, 34, 36 or 38; and (b) a second nucleotide sequence encoding a second amino acid sequence having a transactivation domain wherein the second amino acid sequence is SEQ ID NO:11, 13, 90-96 or 97 or a functional fragment of SEQ ID NO:11, 13, 90-96 or 97 wherein the fusion protein capable of activating transcription of a heterologous polynucleotide that is operably linked to a LexA operator. In one embodiment, the promoter functional in a plant cell is a tissue-specific promoter. In one embodiment, the promoter functional in a plant cell is an inducible promoter.

In one embodiment, the fusion protein encoded by this recombinant DNA construct is capable of activating transcription of a heterologous polynucleotide operably linked to a minimal promoter and at least one LexA operator sequence; and further wherein the heterologous polynucleotide encodes a heterologous polypeptide capable of modifying an agronomic characteristic in the plant cell.

In one embodiment, the at least one LexA operator sequence comprises at least one sequence selected from the group consisting of: a recA-type operator sequence and a caa-type operator sequence.

In one embodiment, the recA-type operator sequence comprises the sequence given in SEQ ID NO:22 and the caa-type operator sequence comprises the sequence given in SEQ ID NO:23.

In one embodiment, the transactivator domain is operably linked to a nuclear localization sequence (NLS). The transactivator domain may be from a CBF protein.

In one embodiment, the NLS comprises the sequence of SEQ ID NO:39.

In another embodiment, this invention concerns a vector, cell, plant, or seed comprising at least one of the recombinant DNA constructs described in the present invention.

One embodiment of the present invention is a method of regulating the expression of a heterologous polynucleotide in a plant, wherein the method comprises the steps of: (a) obtaining a plant comprising a first recombinant DNA construct comprising a promoter functional in a plant cell operably linked to a polynucleotide encoding a fusion protein as described herein, and a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; and (b) growing the plant of step (a) under conditions in which the first recombinant DNA construct is expressed.

One embodiment of the present invention is a method of regulating the expression of a heterologous polynucleotide in a plant, wherein the method comprises the steps of: (a) obtaining a plant comprising a first recombinant DNA construct comprising a promoter functional in a plant cell operably linked to a polynucleotide encoding a fusion protein as described herein; (b) introducing into the plant of step (a) a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; and (c) growing the plant under conditions in which the first recombinant DNA construct is expressed.

One embodiment of the present invention is a method of regulating the expression of a heterologous polynucleotide in a plant, wherein the method comprises the steps of: (a) obtaining a plant comprising a heterologous polynucleotide operably linked to a minimal promoter and at least one LexA operator sequence, wherein the heterologous polynucleotide encodes a heterologous polypeptide capable of modifying an agronomic characteristic in the plant cell; (b) introducing into the plant of step (a) a second recombinant DNA construct comprising a promoter functional in a plant cell operably linked to a polynucleotide encoding a fusion protein as described herein; and (c) growing the plant of step (b) under conditions in which the second recombinant DNA construct is expressed.

One embodiment of the present invention is a method of regulating the expression of a heterologous polynucleotide in a plant, wherein the method comprises the steps of: (a) introducing into a regenerable plant cell a first recombinant DNA construct comprising a promoter functional in a plant cell operably linked to a polynucleotide encoding a fusion protein as described herein, and a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; (b) regenerating a transgenic plant from the regenerable plant cell of step (a) wherein the transgenic plant comprises in its genome the first recombinant DNA construct and the second recombinant DNA construct; and (c) growing the transgenic plant of step (b) under conditions in which the first recombinant DNA construct is expressed. The first and the second recombinant DNA constructs of step (a) may be introduced into the regenerable plant cell sequentially or simultaneously.

One embodiment of the present invention is a method of regulating the expression of a heterologous polynucleotide in a plant, wherein the method comprises the steps of: (a) introducing into a regenerable plant cell a first recombinant DNA construct comprising a promoter functional in a plant cell operably linked to a polynucleotide encoding a fusion protein as described herein, and a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; (b) regenerating a transgenic plant from the regenerable plant cell of step (a) wherein the transgenic plant comprises in its genome the first recombinant DNA construct and the second recombinant DNA construct; and (c) obtaining a progeny plant derived from the transgenic plant of step (b), wherein the progeny plant comprises in its genome the first recombinant DNA construct and the second recombinant DNA constructs described herein; and (d) growing the progeny plant under conditions in which the first recombinant DNA construct is expressed. The first and the second recombinant DNA constructs of step (a) may be introduced into the regenerable plant cell sequentially or simultaneously.

In one embodiment, the invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In another embodiment, the plant comprising the recombinant constructs described in the other embodiments is selected from the group consisting of: *Arabidopsis*, maize, soybean, sunflower, sorghum, canola, mustard, wheat, alfalfa, cotton, rice, barley, millet, sugar cane and switchgrass.

In another embodiment, the present invention concerns a cell, a microorganism, a plant, and a seed comprising any of the recombinant DNA constructs described herein. The cell may be eukaryotic, e.g., a yeast, insect or plant cell, or prokaryotic, e.g., a bacterial cell. The microorganism may be *Agrobacterium*, e.g. *Agrobacterium tumefaciens* or *Agrobacterium rhizogenes*. One embodiment is a method for regulating the expression of a heterologous polynucleotide in a cell (or microorganism) comprising introducing into the cell (or microorganism) with the recombinant DNA constructs of the present invention. The cell (or microorganism) comprising the recombinant DNA construct is also included. In particular embodiments, the cell is eukaryotic cell, e.g., a yeast, insect or plant cell, or prokaryotic, e.g., a bacterial cell. The microorganism may be *Agrobacterium*, e.g. *Agrobacterium tumefaciens* or *Agrobacterium rhizogenes*.

In one embodiment, the promoter operably linked to the fusion protein is a constitutive promoter. In one embodiment, the promoter is a tissue specific promoter. In one embodiment, the promoter is a developmentally regulated promoter. In one embodiment, the promoter is an inducible promoter. Thus, in accordance with the present invention any promoter can be used for regulating the expression of the fusion protein. The choice of promoter depends on the experimental goal. In another embodiment, the transactivation construct containing the fusion protein is operatively linked a splice acceptor sequence. Splice acceptor sequences are well known to skilled artisans. In one embodiment, other regulatory elements that can modulate expression of the chimeric transcriptional activator can be operably linked to it.

In another embodiment of the present invention, a recombinant DNA construct of the present invention comprises other regulatory sequences. In one embodiment of the invention, a recombinant construct of the present invention comprises an enhancer or silencer.

In one embodiment, the present invention provides recombinant constructs for use in expressing heterologous polynucleotides of interest in transgenic plants. In one embodiment, the construct comprises at least one LexA operator sequence, a promoter and a heterologous polynucleotide of interest wherein the operator sequence, the heterologous polynucleotide and the promoter are operably linked to each other. In one embodiment, the LexA operator is a caa operator. In one embodiment, the LexA operator is a recA operator. In one embodiment, the LexA operator comprises multiple adjacent copies (in tandem, separated by a few nucleotides, or overlapping) of the caa operator sequence. In one embodiment, the LexA operator comprises multiple adjacent copies (in tandem, separated by a few nucleotides, or overlapping) of the recA operator sequence. In another embodiment, the LexA operator is a recA operator that is modified or changed to a different sequence containing LexA binding sites (e.g., LexA, recA operator sequences or consensus). In another embodiment, the LexA operator is a caa operator that is modified or changed to a different sequence containing LexA binding sites (e.g., LexA, caa operator sequences or consensus). In one embodiment, copies of different or non-identical LexA operator sequences may be located adjacently for LexA binding.

In another embodiment, the number of the operator sequences or LexA binding sites can be changed to optimize the performance.

In one embodiment, the operator is a synthetic LexA operator operatively linked to a minimal promoter.

In one embodiment, the fusion protein encoded by this recombinant construct is capable of activating transcription of a heterologous polynucleotide operably linked to a minimal promoter and at least one LexA operator sequence; and further wherein the heterologous polynucleotide encodes a heterologous polypeptide capable of modifying an agronomic characteristic in the plant cell.

In one embodiment, the fusion protein is capable of increasing transcription of a heterologous polynucleotide operably linked to: (a) a promoter functional in a plant cell; and (b) at least one LexA operator sequence; and further wherein the heterologous polynucleotide encodes a heterologous polypeptide capable of modifying an agronomic characteristic in the plant cell.

In another embodiment, the at least one LexA operator sequence comprises at least one sequence selected from the group consisting of: a recA-type operator sequence and a caa-type operator sequence. The at least one LexA operator sequence may be 1, 2, 3, 4, 5, 6, 7, 8, 9, 10, 11, 12, 13, 14, 15, 16, 17, 18, 20, 30, 40 or 50 LexA operator sequences. A recombinant DNA construct with multiple LexA operator sequences may comprise a combination of non-identical LexA operator sequences, such as at least one recA-type operator sequence and at least one caa-type operator sequence.

In another embodiment, this invention concerns a vector, cell, plant, or seed comprising the recombinant DNA constructs described in the present invention.

In one embodiment, the fusion protein in the activator locus recognizes an *E. Coli* LexA binding site that is not found in plant genomes or requires multiple neighboring sites, so that is the transactivator would be unlikely to directly affect the expression of endogenous genes. In one embodiment, the expression of the fusion protein does not adversely affect plant function when expressed at levels required for transactivation.

In one embodiment, the "transactivation system" described herein comprises generation of two different kinds of plant lines. One is referred to herein as the "activator line" or the "driver line" and the other line is referred to herein as the "effector" line. The "activator line" comprises the activator locus and the "effector line" comprises the effector locus comprising the heterologous polynucleotide, the expression of which is regulated by the expression of the chimeric transcriptional activator.

In one embodiment of the invention disclosed herein, a plant line comprising the driver locus is transformed to introduce the effector locus to generate a plant line comprising the driver locus as well as the effector locus.

In one embodiment of the invention disclosed herein, a plant line comprising the effector locus is transformed to introduce the driver locus to generate a plant line comprising the driver locus as well as the effector locus.

Crossing a driver plant line with an effector plant line generates double transgenic offspring capable of expressing the heterologous polynucleotide regulated by the expression of the chimeric transactivator. In one embodiment of the invention, combinatorial experiments can be done for bringing the driver locus and the effector locus together in the same plant: one driver line can be crossed to different effector lines to express different heterologous polynucleotides with the same expression pattern and regulatory control. Conversely, the same effector line can be crossed to various drivers to express one heterologous polynucleotide in different spatiotemporal manner.

In one embodiment, a large number of driver lines with various expression patterns can be easily generated using different enhancers or additional regulatory elements.

In one embodiment, the chimeric transactivator may comprise the LexA N-terminal DNA binding domain. In one embodiment the chimeric transactivator may comprise residues 1-87 of the LexA polypeptide. In one embodiment the chimeric transactivator may comprise the full length LexA polypeptide.

In one embodiment, the use of the transactivation system disclosed herein allows regulated expression of transgenes. In one embodiment, it allows gene stacking and allows expression of these genes without using multiple promoters. In one embodiment, the transactivation system disclosed herein can be used with gene-trap and enhancer trapping systems. In one embodiment, the system of gene expression disclosed herein allows expression of developmentally regulated genes which if expressed otherwise may lead to lethality. In one embodiment, this transactivation system may be used for activation tagging screens for identifying key genes for drought tolerance, yield, nitrogen use efficiency, abiotic stress tolerance, root architecture, etc. This system can also be useful for lead optimization (using a bank of promoters). In one embodiment, this system can be used to regulate the trait-conferring transgene expression differently in successive generations.

There are a number of circumstances in which it is advantageous to use the transactivation compositions and methods disclosed herein. Examples where such transactivation would be advantageous include, but are not limited to, situations where the transgene is likely to compromise plant viability or fertility, when a gene is to be expressed or a mutant phenotype is to be complemented in diverse patterns or at distinct developmental stages. A single transgene can be activated in the desired pattern simply by crossing to pre-existing activator lines or retransforming with existing plasmids.

The present invention encompasses functional fragments and variants of the first amino acid sequence having the DNA-binding domain wherein the first amino acid sequence is SEQ ID NO:15, 32, 34, 36 or 38.

The present invention also encompasses functional fragments and variants of the second amino acid sequence having the transactivation domain wherein the second amino acid sequence is SEQ ID NO:11, 13, 90-96 or 97.

A "functional fragment" as used herein is defined as any subset of contiguous nucleotides of the sequences disclosed herein, that can perform the same, or substantially similar function as the sequences disclosed herein. A "functional fragment" with substantially similar function to a sequence disclosed herein refers to a functional fragment that retains largely the same level of activity as the sequence and exhibits the same pattern of expression as the sequence disclosed.

A "functional fragment" of the DNA-binding domain sequence disclosed herein exhibits DNA-binding activity to a LexA operator sequence.

A "functional fragment" of the transactivation domain sequence disclosed herein exhibits transactivator activity.

A "variant", as used herein, is the sequence of the DNA-binding domain or the transactivator domain or the sequence of a functional fragment of the DNA-binding domain or the transactivator domain containing changes in which one or more amino acids of the original sequence is deleted, added, and/or substituted, while substantially maintaining the function of the sequence disclosed herein. One or more amino acids can be inserted, deleted, or substituted internally to the sequence disclosed herein. Variant domains can be produced, for example, by standard DNA mutagenesis techniques or by chemically synthesizing the variant DNA-binding domain or a portion thereof. Substitutions, deletions, insertions or any combination thereof can be combined to produce a final construct.

A variant polypeptide may have an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to the sequence of the DNA-binding domain or the transactivator domain or the sequence of a functional fragment of the DNA-binding domain or the transactivator domain.

A variant of the DNA-binding domain substantially maintains DNA-binding activity to the LexA operator. A variant of the transactivator domain substantially maintains transactivator activity.

The present invention provides a method to manipulate and improve a plant trait.

In one embodiment, the method entails transforming a first plant with a member of a first pool of driver constructs. Each driver construct includes a chimeric transactivator that is placed under the control of a different promoter so that the expression of the chimeric transactivator can be controlled under different conditions. Further, the method entails transforming a second plant with a member of a second pool of effector constructs.

In one embodiment, the invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In another embodiment, the plant comprising the recombinant constructs, described in any of the above embodiments, is selected from the group consisting of: *Arabidopsis*, maize, soybean, sunflower, sorghum, canola, mustard, wheat, alfalfa, cotton, rice, barley, millet, sugar cane and switchgrass.

In one embodiment, the plant comprising the recombinant DNA constructs is a monocotyledenous plant. In another embodiment, the plant comprising the recombinant DNA constructs is a corn or rice plant.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Preparation of LexA and CBF Recombinant Constructs

Preparation of Genomic DNA from *E. coli*:

Prior to amplification of LexA sequences from *E. coli*, genomic DNA was prepared from a derivative of *E. coli* K12 strain (Strain deleted for araC). Preparation of genomic DNA was accomplished using the PROMEGA® Genomic DNA extraction Kit. Briefly, single colonies of *E. coli* were inoculated from freshly streaked LB agar plates and grown in 3 ml LB broth overnight at 37° C. shaker, and bacterial suspension harvested by centrifugation. *E. coli* genomic DNA was prepared as described in the PROMEGA® WIZARD® Genomic DNA extraction Kit.

*Arabidopsis* Gene Amplification:

*Arabidopsis* cDNA library used for amplification of target cDNA was a single stranded cDNA library pool, prepared from total RNA derived from Columbia ecotype. The first strand cDNA synthesis was performed with oligo dT primer as described by in the SUPERSCRIPT®III cDNA synthesis Kit (INVITROGEN™). To amplify the *E. coli* LexA sequences the following primers sets at the PCR conditions described below. Primer pairs for amplification of *E. coli* LexA and *Arabidopsis* are given in Table 1.

Conditions:

| | |
|---|---|
| *E. coli* Genomic DNA/*Arabidopsis* cDNA (200 ng/50 ng) | 5 µl |
| 10X ExTaq Buffer | 5 µl |
| dNTP mix 2.5 mM each | 4 µl |

-continued

| | |
|---|---|
| Primers 10 µM each (forward + reverse) | 10 µl |
| ExTaq DNA polymerase | 0.5 µl |
| Sterile water | 26.5 µl |

TABLE 1

Primers For Amplification of *E. coli* LexA and *Arabidopsis* DREB genes

| Amplified region | Primer | SEQ ID NOS |
|---|---|---|
| full length LexA gene | Forward | SEQ ID NO: 1 |
| (SEQ ID NO: 20) | Reverse | SEQ ID NO: 2 |
| LexA ORF | Forward | SEQ ID NO: 3 |
| (SEQ ID NO: 14) | Reverse | SEQ ID NO: 4 |
| *Arabidopsis* | Forward | SEQ ID NO: 5 |
| CBF1/DREB1b ORF | Reverse | SEQ ID NO: 6 |
| (SEQ ID NO: 10) | | |
| *Arabidopsis* | Forward | SEQ ID NO: 7 |
| CBF3/DREB1a | Reverse | SEQ ID NO: 8 |
| (SEQ ID NO: 12) | | |

PCR Cycling Conditions for the Amplifications:

| | | |
|---|---|---|
| Step 1 | Initial denaturation | 95° C. for 2 min |
| Step 2 | Denaturation | 94° C. for 45 sec |
| Step 3 | Annealing | 63-55° C. for 1 min (touchdown 1° C./cycle) |
| Step 4 | Elongation | 72° C. for 30 sec |
| Go to Step 2, Repeat 8 times | | |
| Step 5 | Denaturation | 94° C. for 45 sec |
| Step 6 | Annealing | 55° C. for 1 min |
| Step 7 | Elongation | 72° C. for 30 sec |
| Go to Step 5, Repeat 25 times | | |
| Step 8 | Final elongation | 72° C. for 5 min |
| Hold at +4° C. | | |

Following this 2.5 µl of the PCR reaction was loaded in 1% agarose gel for analysis, the gels showed the formation of desired sizes of amplicons. Amplicons were cloned in to PCR®2.1-TOPO®, vector, and transformed into *E. coli* TOP10 cells.

| | |
|---|---|
| PCR reaction mix/Amplicon | 3 µl |
| 1.2M NaCl | 1 µl |
| PCR ®2.1-TOPO ® vector | 0.5 µl |
| Sterile water | 1.5 µl |
| Total | 6.0 µl |

The reaction was incubated at 25° C. for 15 min and transformed into chemically competent *E. coli* cells via heat shock transformation, followed by revival and plating on LB plates supplemented with carbenicillin (50 mg/L) and X-Gal-IPTG for blue-white selection of transformants.

Transformants were analyzed by colony PCR with gene-specific primers, and positives were sequenced with combinations of vector specific and gene specific primers. Analysis of sequence was performed using software application in SEQUENCHER® and VECTOR NTI®. Amplification, cloning and sequencing revealed the presence of mutation free sequences for AtCBF1 ORF (SEQ ID NO:10; AtCBF3 ORF (SEQ ID NO:12) and *E. Coli* LexAORF (SEQ ID NO:14). Amplification of AtCBF2 was not accomplished in the conditions marked above. The LexAORF (SEQ ID NO:14) sequences; and the AtCBF1 (SEQ ID NO:10) and AtCBF3 (SEQ ID NO:12) sequences were used as templates for subsequent PCR amplifications as source to DNA binding domains and trans-activator sequences.

Creation of Mini-Omega and Cloning in PBLUESCRIPT®KSII:

To support basal expression of transcription and enhance the translation efficiency of downstream gene, a Mini-Ω sequence (SEQ ID NO:21) consisting of a 82 bp CaMV 35S promoter minimal sequence (SEQ ID NO:16), proximal to the transcription start site and 67 bp Tobacco mosaic virus (TMV) derived omega sequences (SEQ ID NO:17) were generated. Due to the smaller molecular size of this sequence, the fragment was derived through oligonucleotide synthesis that was subsequently cloned into the cloning vector PBLUESCRIPT®KSII.

To clone the fragment, synthetic single stranded oligonucleotides (Oligo core primers) MiniCorePromU (SEQ ID NO:18) and MiniCorePromL (SEQ ID NO:19) were mixed in equimolar ratios (5 µM each) and annealed, followed by amplification with DNA polymerase as described below to complete the fill-in reaction.

| | |
|---|---|
| Oligo core primers 5 µM each | 2 µl |
| 5X DNA polymerase buffer | 10 µl |
| dNTP mix | 4 µl |
| Amplification primers* 10 µM each | 10 µl |
| PHUSION ® HF polymerase | 1 µl |
| Sterile water make up to | 50 µl |

In addition to the amplicons, overlapping primer pairs (amplification primer fwd (AmpliPromF; SEQ ID NO:87) and amplification primer reverse (AmpliPromR; SEQ ID NO:88) were used to both amplify and append restriction sites to the mini promoter TMV omega fragment that would facilitate cloning.

PCR cycles for the reaction were:

| | | |
|---|---|---|
| Step 1 | Initial denaturation | 95° C. for 5 min |
| Step 2 | Denaturation | 94° C. for 45 sec |
| Step 3 | Annealing | 50° C. for 1 min (slow ramp 60%) |
| Step 4 | Elongation | 72° C. for 30 sec |
| Go to Step 2; Repeat 15 times | | |
| Step 5 | Final elongation | 72° C. for 5 min |
| Hold at +4° C. | | |

Following this 2 µl of the amplicon was checked on a 2% agarose gel. The sequences and the engineered restriction sites for the core promoter-TMV omega (MiniΩ) are given in SEQ ID NO:21 and FIG. 1.

To clone the mini-omega sequences, the amplicon (SEQ ID NO:21) was digested with BamHI and XbaI, after PCR purification (QIAGEN® PCR purification kit); following this the fragment was ligated to PBLUESCRIPT®KSII as a directionally, and transformed into E. coli. Transformants were screened with colony PCR, and verified with restriction digestion.

Creation of pBC-Mini Omega GUS-Pin; Mini Promoter-Containing Vector:

To create the pBC-Mini-omega::GUS-Pin construct, the mini promoter-TMV omega sequences (SEQ ID NO:21) were subcloned from Mini-Omega-PBLUESCRIPT®KSII to pBC sans HindIII. Directional cloning was by performed using the BamHI-XbaI sited compatible with the mini-omega fragment released from the cloning vector. Presence of insert was verified using digestion with NcoI.

The reporter GUS and PIN and terminator sequences were excised from the vector INDIA3R/PHP31993 as a 2442 bp HindIII fragment. This was ligated to the pBC Mini-omega backbone (intermediate clone), that was restricted with HindIII.

Being a non-directional cloning, the orientation of the insert was checked by digestion with the asymmetric site BamHI. The mini-omega::GUS clone was sequenced using both vector specific primers as well as primers designed within the GUS and PIN sequences to verify the construct.

Multimerization of Operators to Form Direct Repeats and Cloning of Operators to Generate Various Operator-MiniΩ:GUS Constructs:

To create the various operator core sequences the following oligonucleotide pairs were synthesized to obtain RecA Operator dimer (recA operator single unit is given in SEQ ID NO:22). Caa Operator dimer (Caa operator single unit is given in SEQ ID NO:23). Hybrid Operator (2× Caa type operator+2× RecA type operator) is given in SEQ ID NO:24.

These operators were cloned into pCR2.1 (for the multimers of RecA and Caa type operators) or into PBLUESCRIPT®KSII (in case of the hybrid operator). The details for each are described below.

Multimerization of the RecA type operator was accomplished through a PCR driven multimerization reaction. To achieve multimerization a dimer of RecA was synthesized, and multimer formation was though partial annealing, followed by fill-in reaction at each iteration of PCR. The PCR mediated multimerization reaction is described below. The oligonucleotides used were RecAopU (SEQ ID NO:25) and RecAopL (SEQ ID NO:26).

| | |
|---|---|
| Oligonucleotides mix 10 µM each | 10 µl |
| Sterile water | 15 µl |
| Hot start master mix (QIAGEN ®) | 25 µl |
| Total | 50 µl |

PCR conditions for the reaction were:

| | | |
|---|---|---|
| Step 1 | Initial denaturation | 95° C. for 5 min |
| Step 2 | Denaturation | 94° C. for 45 sec |
| Step 3 | Annealing | 55° C. for 5 sec |
| Step 4 | Elongation | 72° C. for 10 sec |
| Go to Step 2; Repeat 35 times | | |
| Step 5 | Final elongation | 72° C. for 5 min |
| Hold at +4° C. | | |

Reaction was performed with or without 2% DMSO at final concentration

Subsequently, 5 µl of the above reaction were loaded on an agarose gel and analyzed for the formation of higher order multimers.

To clone and screen RecA type operator multimers, the PCR amplicons were cloned in PCR®2.1-TOPO®, and transformed in to E. coli cells. Putative multimers were identified and sorted by colony PCR using vector specific M13F and M13R primers. The formation of RecA multimers was verified using sequence analysis Caa type operator was formed by annealing two partially complimentary oligo-nucleotide sequences. To create a double stranded fragment, the annealed oligonucleotide that was provided a T/A overhang using a Taq DNA polymerase reaction as described below, the sequences of the oligonucleotides are given in SEQ ID NO:27 (CaaOpU) and SEQ ID NO:28 (CaaOpL).

| | |
|---|---|
| Oligonucleotides mix 10 μM each | 10 μl |
| Sterile water | 15 μl |
| Hot start master mix (QIAGEN ®) | 25 μl |
| Total | 50 μl |

PCR conditions for the reaction were

| | | |
|---|---|---|
| Step 1 | Initial denaturation | 95° C. for 5 min |
| Step 2 | Denaturation | 94° C. for 45 sec |
| Step 3 | Annealing | 25° C. for 1 min (Slow ramp 20%) |
| Step 4 | Elongation | 72° C. for 1 min |
| Go to Step 2; Repeat 5 times | | |
| Step 5 | Final elongation | 72° C. for 20 min |
| Hold at +4° C. | | |

The formation of desired 100 bp fragment was confirmed by loading 2.5 μl of the reaction in a 2% agarose gel.

The Caa type operator dimer was cloned into pCR®2.1-TOPO® vector and transformed in to E. coli cells. Putative clones were identified by colony PCR using vector specific M13F and M13R primers. The formation of caa type operator dimer was verified by sequencing.

To create the hybrid operator, consisting of both RecA type and Caa type operators, two partially complementary oligonucleotides were designed. To create a double stranded fragment, the annealed oligonucleotide was filled-in using a polymerase as described below, the sequences of the oligonucleotides are given in SEQ ID NO:29 (HybOpUhalf) and SEQ ID NO:30 (HybOpLHalf).

| | |
|---|---|
| Oligonucleotides mix 10 μM each | 10 μl |
| Sterile water | 15 μl |
| Hot start master mix (QIAGEN ®) | 25 μl |
| Total | 50 μl |

PCR conditions for the reaction were:

| | | |
|---|---|---|
| Step 1 Initial denaturation | | 95° C. for 5 min |
| Step 2 Denaturation | | 94° C. for 45 sec |
| Step 3 Annealing | | 50° C. for 30 sec |
| Step 4 Elongation | | 72° C. for 30 sec |
| Go to Step 2; Repeat 25 times | | |
| Step 5 Final elongation | | 72° C. for 5 min |
| Hold at +4° C. | | |

The formation of the desired 100 bp fragment was confirmed by loading 2.5 μl of the reaction in a 2% agarose gel.

The Hybrid type operator was PCR purified, restriction digested with EcoRI and BamHI, and ligated into Mini-Omega-pBLUESCRIPT®KSII, to create Hybop-MiniOmega fragment. E. coli transformants were identified with colony PCR using vector specific M13F and M13R primers.

Generation of Operator::GUS Constructs:

The operator multimers for RecA type operator or Caa type operator were excised from their cloning vector backbones as EcoRI fragments and were cloned into the EcoRI site of the basal operator-less vector MiniΩ::GUS.

Ligation reaction for these reactions was performed using 1:50 to 1:100 molar ratios of vector to insert:

| | |
|---|---|
| pBC MinΩ::GUS EcoRI cut, dephosphorylated vector | 2 μl (10-20 ng) |
| Insert (Op multimer fragments) | 4 μl (200-400 ng) |

-continued

| | |
|---|---|
| 10X T4 DNA ligase buffer with rATP | 1 μl |
| Sterile water | 2 μl |
| T4 DNA ligase | 1 μl |
| Total | 10 μl |

To obtain the construct Hybop-MinΩ::GUS the Hybrid-type operator sequences were excised from pBLUESCRIPT®KSII, or the Caa type operator or RecA type operators were mixed in equimolar ratios and ligated at the EcoRI site upstream to mini-promoter-Omega::GUS sequences. Ligation reaction were transformed into E. coli XL1-BLUE® cells and plated on LB plates supplemented with Kanamycin.

To screening of operator-MinΩ::GUS clone, core promoter specific primer pairs and pBC backbone specific primer pairs were used in colony PCR. Putative operator-mini omega::GUS transformants were selected, size-sorted for operator multimers that were subsequently validated by sequence analysis Generation of Several Combinations of DNA-Binding Domain—Transactivator Fusion Proteins:

Driver constructs with LexA-derived DNA binding domain and trans-activation regions were essential created by fusion PCR. Efficient fusion was accomplished by use of method of using GC-rich linker sequences (disclosed in Patent Application No. PCT/US2011/050191) to enable accurate gene fusion. Variants for DNA binding are given below, and in Table 2.
 a) LexAwt1-87 aa DBD (SEQ ID NO:31; amino acid sequence SEQ ID NO:32)
 b) LexA 1-87MNF, with engineered NLS and Gly-Ala cleavage blocked mutant (LexA MNF; SEQ ID NO:33 and amino acid sequence SEQ ID NO:34)
 c) LexA 1-202 full length (LexAFL; SEQ ID NO:35) with cleavage blocked mutant (LexAmut FL; and amino acid sequence SEQ ID NO:36).
 d) LexA 1-202 full length (LexAFLNLS), cleavage blocked, containing NLS engineered in loop (LexAmutFL NLS; SEQ ID NO:37; amino acid sequence SEQ ID NO:38).

The deletion sequence and mutations engineered within LexA and the rationale for their consideration to create trans-activators have been marked below:
 a) The N terminal 1-87 amino-acid region has been shown to be involved in DNA binding. This region has been used for create LexA-VP16 based induction systems.
 b) The LexA DNA binding region displays auto-cleavage, at the Ala-Gly bond. $G_{85}$ to D mutation stabilized this bond from cleavage in full length LexA protein. In addition to this mutation an NLS has been introduced at the domain linker region, to enhance nuclear localization of the fusions.
 c) LexA full length protein has been shown to bind at higher affinity, as a protein dimer to its operator sequences with high binding affinity. However, native LexA protein displays autocatalytic cleavage. To stabilize the full length LexA protein auto-cleavage mutations were generated. Besides these mutations silent mutation to remove an EcoRV site for facilitating molecular cloning has been engineered. The various mutations generated are described in detail below.
 d) LexA full-length protein stabilized for auto-cleavage has been engineered to include mutation at E71-K, that has been shown to enhance DNA binding, as well as insert an eukaryotic NLS consensus KKRK (SEQ ID NO:100), in a loop region of the LexA protein.

A summary of the various mutations engineered into the LexA domain is given in the Table 2 given below.

TABLE 2

Summary of LexA Modifications

| No. | Name of LexA Variant | Description of Variant | SEQ ID NO (nt) | SEQ ID NO (amino acid) |
|---|---|---|---|---|
| a | LexA 1-87(wt) | The N terminal 1-87 amino-acid region as DBD | 31 | 32 |
| b | LexAMNF | i. Mutation of Gly to Asp (G85-D85)<br>ii. Added NLS | 33 | 34 |
| c | LexAFL | i. Mutation of Gly to Asp (G85-D85)<br>ii. Mutation of Ser 119 to Ala<br>iii. No NLS sequence | 35 | 36 |
| d | LexAFLNLS | i. Mutation of Gly to Asp (G85-D85)<br>ii. Mutation of Ser 119 to Ala<br>iii. Addition of Mutation E71 to K<br>iv. Added NLS | 37 | 38 |

Trans-activator fusion comprised of various deletions of the plant DREB/CBF sequences derived from the hydrophobic cluster region. The sequences taken for creation of trans-activators are given in Table 3.

TABLE 3

Starting and Ending Nucleotide Positions of CBF Fragments

| CBF Fragment | Length | Transactivator Region | Domains Included | SEQ ID NO (nt) | SEQ ID NO (aa) |
|---|---|---|---|---|---|
| CBF1A | 297 | 1-297 bp | HC1-HC6 | 40 | 90 |
| CBF1B | 258 | 1-258 bp | HC1-HC5 | 41 | 91 |
| CBF1C | 222 | 1-222 bp | HC1-HC4 | 42 | 92 |
| CBF1D | 183 | 1-183 bp | HC1-HC3 | 43 | 93 |
| CBF1E | 126 | 130-255 bp | HC2-HC5 | 44 | 94 |
| CBF1F | 114 | 130-243 bp | HC2-HC4 | 45 | 95 |
| CBF1G | 156 | 139-294 bp | HC2-HC6 | 46 | 96 |
| CBF3I | 213 | 1-213 bp | HC1-HC6 | 47 | 97 |

Fusion fragments marked A-G (SEQ ID NOS:40-46 respectively) are derived from AtCBF1/AtDREB1b and fragment I (SEQ ID NO:47) is derived from the AtCBF3/AtDREB1a sequences. The nucleotide sequences for these selected sequences and their protein translations are given in Table 3.

Example 2

Recombinant Driver Fusion Constructs

Creation of LexA1-87 DBD-CBF Fusions:

Generation of fusion proteins was accomplished by a modified overlap fusion PCR based approach that involved two PCR amplification reactions. The linker sequences comprised of the GC rich sequences.

In the first step LexA 1-87 domain (SEQ ID NO:31) was amplified and the various deletions of CFB1/CBF3 were individually amplified with the primer pair listed below Table 4.

TABLE 4

Primer Sequences for Amplifying LexA 1-87 and CBF Fragments

| Amplified region | Primer | SEQ ID NOS |
|---|---|---|
| LexA 1-87 region | Forward | 48 |
| | Reverse | 89 |
| CBF1_Fragment A | Forward | 49 |
| | Reverse | 50 |
| CBF1_Fragment B | Forward | 49 |
| | Reverse | 51 |
| CBF1_Fragment C | Forward | 49 |
| | Reverse | 52 |
| CBF1_Fragment D | Forward | 49 |
| | Reverse | 53 |
| CBF1_Fragment E | Forward | 54 |
| | Reverse | 55 |
| CBF1_Fragment F | Forward | 54 |
| | Reverse | 55 |
| CBF1_Fragment G | Forward | 56 |
| | Reverse | 50 |
| CBF3_Fragment I | Forward | 57 |
| | Reverse | 58 |

PCR amplification components for the primary reaction were:

| Template | 10-100 ng |
|---|---|
| 5X PHUSION ® HF buffer | 1X final |
| dNTP 10 mM | 0.05 mM each final |
| DMSO | 2% final |
| Betaine 5M | 1M final |
| Primers | 0.2-0.4 µM |
| Water | Final volume 50 µM |
| PHUSION ® polymerase | 2 Units |

PCR Reaction Conditions:

| Step1 94° C. | 2 min |
|---|---|
| Step2 94° C. | 1 min |
| Step3 63-58° C. | 1 min (Touch down 1° C./cycle) |
| Step4 68° C. | 1 min/kb |
| Go to Step 2, Repeat 6 times | |
| Step5 94° C. | 45 sec-60 sec |
| Step6 55° C. | 30 sec-60 sec |
| Step7 72° C. | 1 min/kb |
| Go to Step 5, Repeat 22-25 times | |
| Step8 72° C. | 5-10 min |
| Hold at 4° C. | |

2.5 µl of reaction were checked on a 2% agarose gel, and appropriately sized amplicons representing each deletion were recovered via gel elution (QIAGEN®).

To achieve gene fusions, gel purified amplicons representing the various fragments (A-G and I; SEQ ID NOS: 40-46 and SEQ ID NO:47 respectively); were mixed with purified amplicon for the LexA 1-87 region, and amplified using the following conditions. Primer combinations used in the creation of the fusions are common to all the domain fusions described for all the different LexA-CBF fusions that have been given below in Table 5.

TABLE 5

Primers for Fusion Construct PCR of LexA1-87 and CBF Fragments

| S.No. | Fusion Construct | Fwd Primer (SEQ ID NO) | Rev Primer (SEQ ID NO) |
|---|---|---|---|
| 1 | LexA1-87-CBF1A | 48 | 50 |
| 2 | LexA1-87-CBF1B | 48 | 51 |

TABLE 5-continued

Primers for Fusion Construct PCR of LexA1-87 and CBF Fragments

| S.No. | Fusion Construct | Fwd Primer (SEQ ID NO) | Rev Primer (SEQ ID NO) |
|---|---|---|---|
| 3 | LexA1-87-CBF1C | 48 | 52 |
| 4 | LexA1-87-CBF1D | 48 | 53 |
| 5 | LexA1-87-CBF1E | 48 | 51 |
| 6 | LexA1-87-CBF1F | 48 | 55 |
| 7 | LexA1-87-CBF1G | 48 | 50 |
| 8 | LexA1-87-CBF3I | 48 | 58 |

PCR amplification for the fusion was done under the conditions:

| | |
|---|---|
| Amplicons (Domain A + Domain B) | 10-100 ng |
| 0.1-1:0.1-1 molar ratio of Domain A to Domain B | |
| 5X PHUSION ® HF buffer | 1X final |
| dNTP 10 mM | 0.05 mM final |
| DMSO | 2% final |
| Betaine 5M | 1M final |
| Primer A/Primer B | 0.2-0.4 µM |
| Primer A'/Primer B' | 0.2-0.4 µM |
| Water | To final volume 50 µM |
| PHUSION ® polymerase | 2 Units |

PCR Reaction Conditions:

| | |
|---|---|
| Step 1 94° C. | 2 min |
| Step 2 94° C. | 45 sec-60 sec |
| Step 3 60-62° C. | 30 sec-60 sec |
| Step 4 72° C. | 1 min/kb (final size) |
| Go to Step 2, | Repeat 20-25 times |
| Step 5 | 72° C.; 5-10 min |
| Hold at 4° C. | |

2.5 µl of reaction were checked on a 1.5% agarose gel, to determine the formation of fused sequences based on their molecular sizes.

Creation of LexAMNF-CBF Fusions:

To engineer this driver fusion, first step of amplification for LexA 1-87 domain with the 3' reverse primer, containing sequences that encoded a eukaryotic NLS, as well as the linker sequences were predicted to display flexibility. This amplicon was fused to the deletions of CFB1/CBF3 that were individually amplified with the primer pair listed below Table 6.

TABLE 6

Primers for Amplifying Fragments for LexAMNF-CBF Fusions:

| Amplified region | Primer | SEQ ID NO |
|---|---|---|
| LexA MNF | Forward | 48 |
| | Reverse | 59 |
| CBF1_Fragment A | Forward | 60 |
| | Reverse | 61 |
| CBF1_Fragment B | Forward | 60 |
| | Reverse | 62 |
| CBF1_Fragment C | Forward | 60 |
| | Reverse | 63 |
| CBF1_Fragment D | Forward | 60 |
| | Reverse | 64 |
| CBF1_Fragment E | Forward | 65 |
| | Reverse | 62 |
| CBF1_Fragment F | Forward | 65 |
| | Reverse | 66 |
| CBF1_Fragment G | Forward | 67 |

TABLE 6-continued

Primers for Amplifying Fragments for LexAMNF-CBF Fusions:

| Amplified region | Primer | SEQ ID NO |
|---|---|---|
| | Reverse | 61 |
| CBF3_Fragment I | Forward | 68 |
| | Reverse | 69 |

PCR amplification conditions were:

| | |
|---|---|
| Template | 10-100 ng |
| 5X PHUSION ® HF buffer | 1X final |
| dNTP 10 mM | 0.05 mM each final |
| DMSO | 1-2% final |
| Betaine 5M | 1M final |
| Primers | 0.2-0.4 µM |
| Water | To final volume |
| PHUSION ® polymerase | 1-2 Units |

PCR Reaction Conditions:

| | |
|---|---|
| Step 1 94° C. | 2 min |
| Step 2 94° C. | 1 min |
| Step 3 63-58° C. | 1 min (Touch down 1° C./cycle) |
| Step 4 68° C. | 1 min/kb |
| Go to Step 2, | Repeat 6 times |
| Step 5 94° C. | 45 sec-60 sec |
| Step 6 55° C. | 30 sec-60 sec |
| Step 7 72° C. | 1 min/kb |
| Go to Step 5, | Repeat 22-25 times |
| Step 8 72° C. | 5-10 min |
| Hold at 4° C. | |

2.5 µl of reaction were checked on a 2% agarose gel, and appropriately sized amplicons representing each deletion were recovered via gel elution (QIAGEN®).

To achieve gene fusions, gel purified amplicons representing the various fragments (A-G and I); were mixed with purified amplicon for the LexAMNF region containing the appended NLS sequence, and amplified using the following conditions. Primer combinations used in the amplification were similar to the primer combinations marked above in the fusion PCR section described for the LexA1-87-CBF fusions (see Table 5). Subsequent to fusion PCR, 2.5 µl of reaction were checked on a 1.5% agarose gel, to determine the formation of fused sequences based on their molecular sizes.

Creation of LexAFL-CBF Fusions:

To engineer this driver fusion, first step required the creation of site-directed mutations in the LexA gene, prior to generation of sequence fusion. Site-directed mutation was through overlap PCR approach. For creating the site directed mutations, wild-type LexA gene template was amplified as three overlapping fragments (fragments 1, 2 and 3, given below), encompassing the mutations. The map of the fragment is described above with the description of the mutation. The PCR conditions for creating these fragments and the primer pairs are marked below

TABLE 7

Primers for Overlapping Fragments 1-3 for LexAFL

| Amplified region | Primer | SEQ ID NO |
|---|---|---|
| Fragment 1 | Forward | 48 |
| | Reverse | 70 |

TABLE 7-continued

Primers for Overlapping Fragments 1-3 for LexAFL

| Amplified region | Primer | SEQ ID NO |
|---|---|---|
| Fragment 2 | Forward | 71 |
|  | Reverse | 72 |
| Fragment 3 | Forward | 74 |
|  | Reverse | 75 |

PCR conditions for amplification were:

| Template | 10-100 ng |
|---|---|
| 5X PHUSION ® HF buffer | 1X final |
| dNTP 10 mM | 0.05 mM each final |
| DMSO | 1-2% final |
| Betaine 5M | 1M final |
| Primers | 0.2-0.4 µM |
| Water | To final volume |
| PHUSION ® polymerase | 1-2 Units |

PCR Reaction Conditions:

| Step 1 94° C. | 2 min |
|---|---|
| Step 2 94° C. | 1 min |
| Step 3 63-58° C. | 1 min (Touch down 1° C./cycle) |
| Step 4 68° C. | 1 min/kb |
| Go to Step 2, | Repeat 6 times |
| Step 5 94° C. | 45 sec-60 sec |
| Step 6 55° C. | 30 sec-60 sec |

Subsequently, overlap extension based PCR was used to create the desired site-directed LexA full-length mutant sequences that were assembled by mixing equimolar amounts of the three amplicons (fragment1+fragment 2+fragment 3), and amplified with the primer sets.

Overlap PCR Primer Set for LexAFL:

```
Fwd primer (SEQ ID NO: 48):
5'-AGACTCGAGATGAAAGCGTTAACGGCCAGG-3'

Rev. Primer (SEQ ID NO: 74):
5'-GGGCGCGCCGGCGCCCAGCCAGTCGCCGTTGCGAATA-3'
```

Subsequently, the reaction was analyzed by to determine the formation of appropriate sized amplicons.

To obtain fusion proteins for LexA full-length containing the engineered mutations (LexAFL), was amplified with 3' reverse primer, containing sequences predicted to display flexibility, represented by the type II linker sequences (described in Patent Application No. PCT/US2011/050191). The reconstituted LexA full-length (LexAFL) amplicon was fused to the CFB1/CBF3 fragments (A-G and I; SEQ ID NO:40-46 and 47 respectively), containing the Type II linker tag, that were individually amplified with the same primer pairs as above in Table 5. 2.5 µl of reaction were checked on a 2% agarose gel, and appropriately sized amplicons representing each deletion were recovered via gel elution (QIAGEN®).

Creation of LexAFLNLS-CBF Fusions:

To engineer this driver fusion, set, the LexA full-length protein with the mutations described before (LexAFLNLS; SEQ ID NO:37) were used as template to create additional site-directed mutation and insertion mutation of the NLS in a loop region of LexA. The mutations were accomplished by using overlap extension PCR approaches. As a first step LexA sequences were amplified as three overlapping fragments with the following primer sets, to create the fragments 4, 5, and 6. Primer sets used to amplify the fragments were

TABLE 8

Primers for Overlapping Fragments 4-6 for LexAFLNLS

| Amplified region | Primer | SEQ ID NO |
|---|---|---|
| Fragment 4 | Forward | 81 |
|  | Reverse | 82 |
| Fragment 5 | Forward | 83 |
|  | Reverse | 84 |
| Fragment 6 | Forward | 85 |
|  | Reverse | 86 |

Subsequently, the desired site-directed LexA full-length NLS mutant sequences were reconstituted by mixing equimolar amounts of the three amplicons (4+5+6; SEQ ID NOS:78-80 respectively), that was amplified with the primer set marked below:

```
Fwd primer (SEQ ID NO: 81):
5'-AGACTCGAGATGAAAGCGTTAACGGCCAGG-3'

Rev primer (SEQ ID NO: 86):
5'-GGGCGCGCCGGCGCCCAGCCAGTCGCCGTTGCGAATA-3'
```

To obtain fusion proteins for LexA full-length with NLS (LexAFLNLS) containing the additional mutations and NLS and containing sequences predicted to display flexibility, represented by the type II linker sequences. The reconstituted LexA full-length (LexAFLNLS) amplicon was fused to the CFB1/CBF3 fragments (A-G; I (SEQ ID NOS:40-46 and 47 respectively)), containing the Type II linker tag, that were individually amplified with the same primer pairs as above in Table 5. 2.5 µl of reaction were checked on a 2% agarose gel, and appropriately sized amplicons representing each deletion were recovered via gel elution (QIAGEN®).

Example 3

Cloning of the LexA-CBF Fusion Fragments in pBLUESCRIPT®KSII

Figure 3:
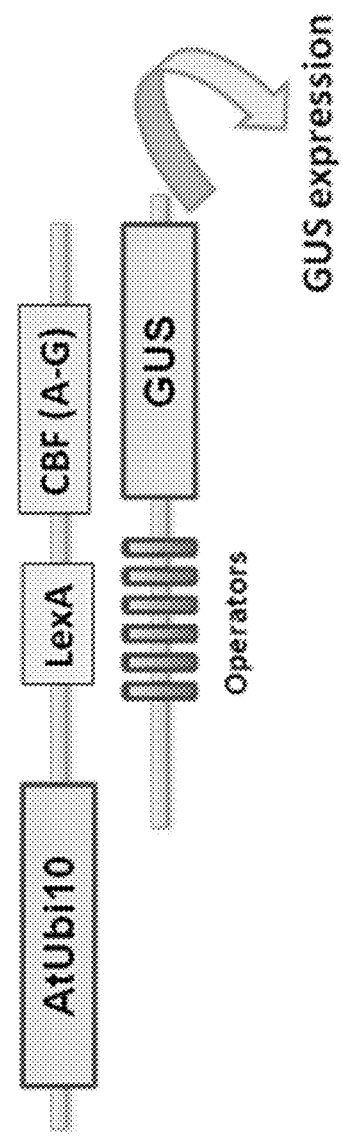
FIG. 3 shows a schematic depicting the mechanism of the transactivation system disclosed in the present invention.

All the LexA-CBF fusion fragments given in Table 9 and the vector were digested with restriction enzymes XhoI and Hind III and later ligated. A schematic representation of the mechanism of two component system is given in FIG. 3.

TABLE 9

LexA-CBF Fusion Fragments

|  | Driver (LexA-CBF) Fusion Fragments |
|---|---|
| 1 | $Lex_{1-87}$DBD-CBF1A |
| 2 | $Lex_{1-87}$DBD-CBF1B |
| 3 | $Lex_{1-87}$DBD-CBF1C |
| 4 | $Lex_{1-87}$DBD-CBF1D |
| 5 | $Lex_{1-87}$DBD-CBF1E |
| 6 | $Lex_{1-87}$DBD-CBF1F |
| 7 | $Lex_{1-87}$DBD-CBF1G |
| 8 | $Lex_{1-87}$DBD-CBF3I |
| 9 | LexA-MNF-CBF1A |
| 10 | LexA-MNF-CBF1B |
| 11 | LexA-MNF-CBF1C |
| 12 | LexA-MNF-CBF1D |
| 13 | LexA-MNF-CBF1E |
| 14 | LexA-MNF-CBF1F |
| 15 | LexA-MNF-CBF1G |

TABLE 9-continued

LexA-CBF Fusion Fragments

| | Driver (LexA-CBF) Fusion Fragments |
|---|---|
| 16 | LexA-MNF-CBF3I |
| 17 | LexA-FL-CBF1A |
| 18 | LexA-FL-CBF1B |
| 19 | LexA-FL-CBF1C |
| 20 | LexA-FL-CBF1D |
| 21 | LexA-FL-CBF1E |
| 22 | LexA-FL-CBF1F |
| 23 | LexA-FL-CBF1G |
| 24 | LexA-FL-CBF3I |
| 25 | LexA FLNLS-CBF1A |
| 26 | LexA FLNLS-CBF1B |
| 27 | LexA FLNLS-CBF1C |
| 28 | LexA FLNLS-CBF1D |
| 29 | LexA FLNLS-CBF1E |
| 30 | LexA FLNLS-CBF1F |
| 31 | LexA FLNLS-CBF1G |
| 32 | LexA FLNLS-CBF3I |

Plating of the Transformed Cells:

The transformed cells were centrifuged at 4000 rpm for 4-5 minutes. The supernatant was discarded (retaining 200 µl of the media). The cells were resuspended and then plated on LB plates with X-gal and IPTG added in the medium for blue white selection. Carbenicillin was the selection marker added. For analysis of XL1-BLUE® clones colony PCR analysis was performed in 96 well microtitre plates or PCR strips (Axygen, USA). Single, XL1-BLUE® transformants, growing on antibiotic carbenicillin supplemented LB-agar plates were individually picked and patched onto LB-Agar carbenicillin plates and then dropped into 5 µl of sterile water. A total of 12 clones were screened for each ligation reaction done, and in each instance M13 forward and reverse primers were used for screening the clones.

Colony PCR set up is detailed below:

| Sterile water containing colony | 4 µl |
|---|---|
| M13 Forward primer (10 µM) | 0.5 µl |
| M13 Reverse primer (10 µM) | 0.5 µl |
| HSSM | 5 µl |
| Total | 10.0 µl |

PCR Cycling Conditions:

| Step 1 | 95° C. | 5:00 minutes (Initial enzyme activation) |
|---|---|---|
| Step 2 | 94° C. | 00:30 seconds (Denaturation) |
| Step 3 | 55° C. | 00:45 seconds (Annealing) |
| Step 4 | 72° C. | 02:00 minutes (Elongation) |
| Steps 2, 3, 4 iterated 30 times | | |
| Step 5 | 72° C. | 15:00 minutes (Final elongation) |
| Hold at | 16° C. | |

Gel Analysis:

The fused fragments with the vector were then resolved on 1% agarose gels containing DNA visualization dye ethidium bromide. Gel was documented with transmitted UV using AlphaImager system. Image contrast and exposure were corrected using the software.

After analysis of the gel image four positive colonies for each CBF fragment (A, B, C, D, E, F, G and I fusion constructs) were selected from the patched LB-Agar carbenicillin plates and inoculated into culture tubes. The culture tubes contained 6 ml of 2XYT media with 6 µl of carbenicillin antibiotic. They were then incubated in the orbital shaker at 250 rpm at 37° C. overnight. Plasmids were isolated from all the colonies using the Wizard Plus SV Minipreps Plasmid Purification Kit. Instructions as per the protocol provided were followed. The plasmids were eluted in 60 µl of sterile distilled water. The concentrations were checked using the Nanodrop. All the concentrations were found to be of an average of 200 ng/µl. The plasmids were then sent for sequencing to check for any mutations in the length of the fragment. Sequence analysis was performed using analysis software, SEQUENCHER® version 4.7, developed by Gene Codes, USA.

Figure 2:
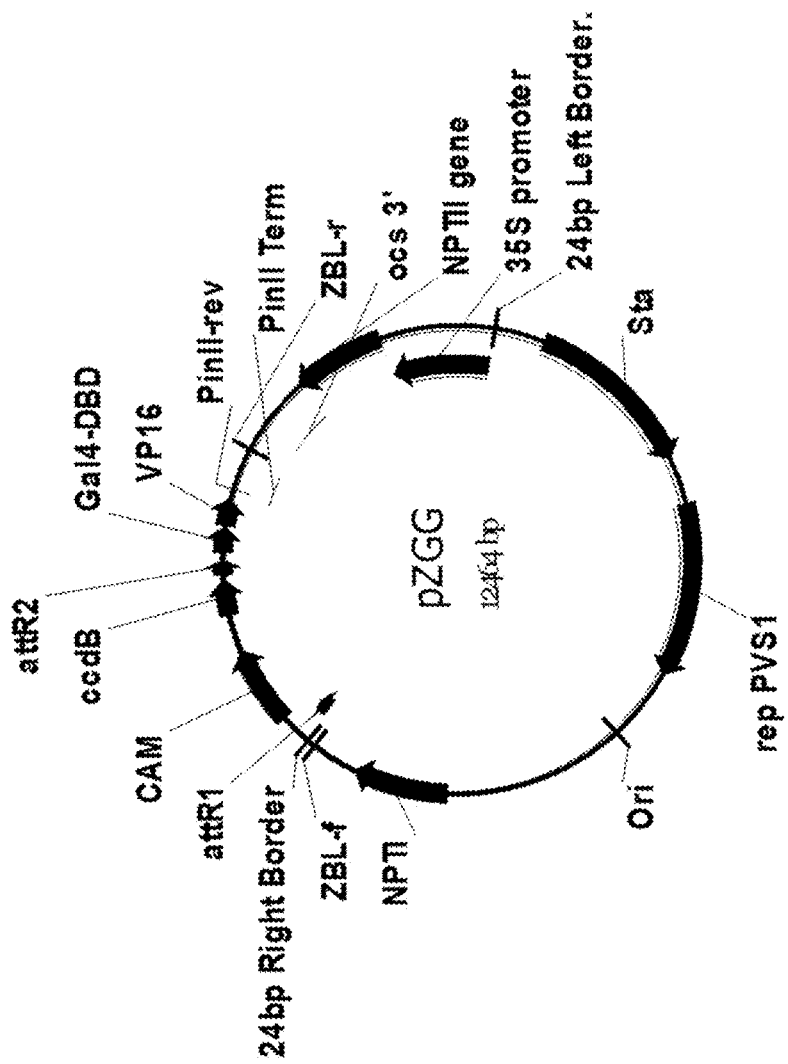
FIG. 2 shows a map of the pZGG vector.

Cloning of the LexA-CBF Fusion Fragments in pZGG Vector:

The LexA-CBF fusions from pBSKSII were cloned in to pZGG binary vector (FIG. 2) and subsequently transformed in to *Agrobacterium tumefaciens*.

Example 4

Development of Operator::Driver Plant Lines

Stable Operator Lines were Developed by Transforming Wild-Type *Arabidopsis* Plants with the Operator Constructs in the Following Way:

About 4-week-old *Arabidopsis* plants with floral buds were dipped in the bacterial suspension of an *Agrobacterium* strain C58 cultured in YEP medium including 5% sucrose and 0.04%-0.05% Silwet-77. Once the plants complete their lifecycle the seeds were harvested. The seeds were collected from these lines and were passed through BASTA® screening. The positive operator *Arabidopsis* lines are then transformed with the driver constructs in the following way:

The harvested operator seeds were sown in the organic soil mixture. Once the seedlings reach two leaf stage three consecutive BASTA® sprays were administered with an interval of 3 days each. The concentration of BASTA® used was 3 mg/liter. The plants were allowed to grow till the flowering stage and used for the transformation with driver constructs. After transformation with the driver constructs these lines were allowed to complete their life cycle and seeds were harvested.

The seeds were dried at room temperature for two weeks and then selected for kanamycin resistance on MS media. The details of the protocol used are given below:

Materials and Methods:
MS Media:
MS media was prepared with the following composition and the pH was set to 5.8.

| MS | 4.5 g/L |
|---|---|
| Sucrose | 8 g/L |
| Vitamin B5 | 1 ml/L |
| BACTO® Agar | 10 g/L |

The media was autoclaved and kanamycin was added in (50 mg/L) concentrations and poured into the plates. The wild-type and the transgenic seeds were surface sterilized with hypochlorite (with Tween 20) and 70% ethanol with the following protocol Surface Sterilization of *Arabidopsis* Seeds:
Materials required:
100% Ethanol
4% Hypochlorite solution
TWEEN®-20
Sterile water 1000 μl micropipette
Table top mini microfuge
Sterile tips for 1000 μl pipette
250 ml plastic beaker
Digital Timer All the steps for surface sterilization were performed in the laminar flow bench.

Transgenic seeds containing driver operator constructs were taken in a 1.7 ml microfuge tube. 1 ml of ethanol was added to each tube and they were inverted a few times to wash the seeds. The ethanol treatment was given for 1:30 minutes, followed by a brief spin in the microfuge such that the seeds settled down and the ethanol could be poured out into the beaker. Wash the seeds with 1 ml sterile water, followed by a brief spin and removal of the water. 1 ml of hypochlorite containing 2% TWEEN®-20 was added to the tubes containing ethanol treated seeds for a 2:30 minute treatment. Hypochlorite was removed and the seeds were washed multiple (4-5) times in sterile water to remove any remnants of detergent. The seeds were suspended in 500 μl of sterile water after the final wash and stratified overnight for two days at 4° C.

The seeds were then inoculated into MS plates supplemented with (50 mg/L) kanamycin. An approximate of 100 μl of *Arabidopsis* seeds are plated in a single plate. The plates were then transferred to the growth chamber.

The seedlings that had grown on the kanamycin selection were selected after 7 days. Positive seedlings were selected based on the green color and survival on the selection media. These were then taken for the assay for both qualitative with GUS histochemical staining and quantitative by fluorescent MUG assay.

TABLE 10

Details for Operator::Driver Transactivator Combinations Taken for Assay

| Driver-Transactivator Construct | Components of Driver-Transactivator Construct | Operator |
|---|---|---|
| Driver4 | pZGG-AtUbi10-LexAMNF-CBF1-A | Control_MiniΩ::GUS |
| Driver4 | pZGG-AtUbi10-LexAMNF-CBF1-A | 6XRecAOP: MiniΩ::GUS |
| Driver4 | pZGG-AtUbi10-LexAMNF-CBF1-A | 2xCaaOP: MiniΩ::GUS |
| Driver4 | pZGG-AtUbi10-LexAMNF-CBF1-A | HybOP: MiniΩ::GUS |
| Driver6 | pZGG-AtUbi10-LexAFL-CBF1-A | Control_MiniΩ::GUS |
| Driver6 | pZGG-AtUbi10-LexAFL-CBF1-A | 6XRecAOP: MiniΩ::GUS |
| Driver6 | pZGG-AtUbi10-LexAFL-CBF1-A | CaaOP: MiniΩ::GUS |
| Driver6 | pZGG-AtUbi10-LexAFL-CBF1-A | HybOP: MiniΩ::GUS |

GUS Histochemical Assay:

GUS assay was done by collecting the leaf tissue by cutting with a pair of sharp scissors and incubated with 200 μl of GUS Histochemical staining solution at 37° C. for overnight in incubator and then imaged, the stained tissue sample after decolorizing the chlorophyll pigment of the sample with 95% ethanol. GUS staining protocol used was as per materials and methods in Jefferson et al., (1987) *EMBO Journal*, vol. 6 no. 13 pp. 3901-3907.

Results for GUS Assay for Operator::Driver-Transactivators:

Histochemical assay images were taken for the positives which has shown GUS expression for the Driver4 and Driver6, with three operators combinations 6xRecAOP: MiniΩ::GUS, 2xCaaOP: MiniΩ::GUS, HybOP: MiniΩ::GUS and Negative Control_MiniΩ::GUS (control doesn't have any operator sequence).

MUG Assay for Driver Transactivators:

The tissues which showed positive results in the GUS assay were selected for the MUG assay. MUG Assay was done by extraction of protein from collected tissue sample and assay was carried out in triplicates for every sample as per the materials and methods in (Richard A. Jefferson, Tony A. Kavanagh and Michael W. Bevan (1987) *EMBO Journal*, vol. 6 no. 13 pp. 3901-3907)

Figure 4:
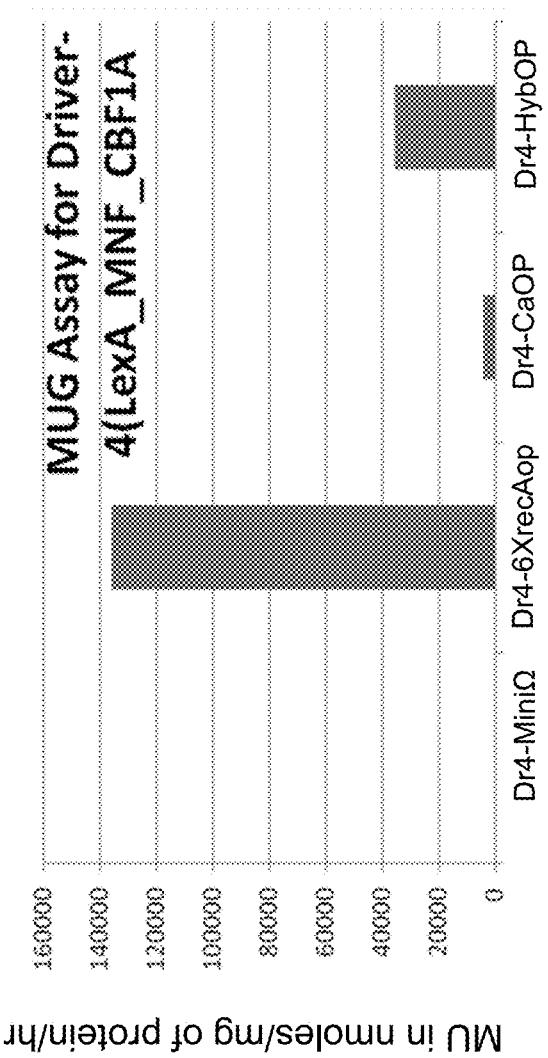
FIG. 4 shows the MUG analysis for Driver 4 with different operator combinations (Driver4 and 6×recA operator, Driver4 and 2×caa operator, Driver4 and hybrid operator) compared to the negative control (Driver4-miniΩ; no operator).
Figure 5:
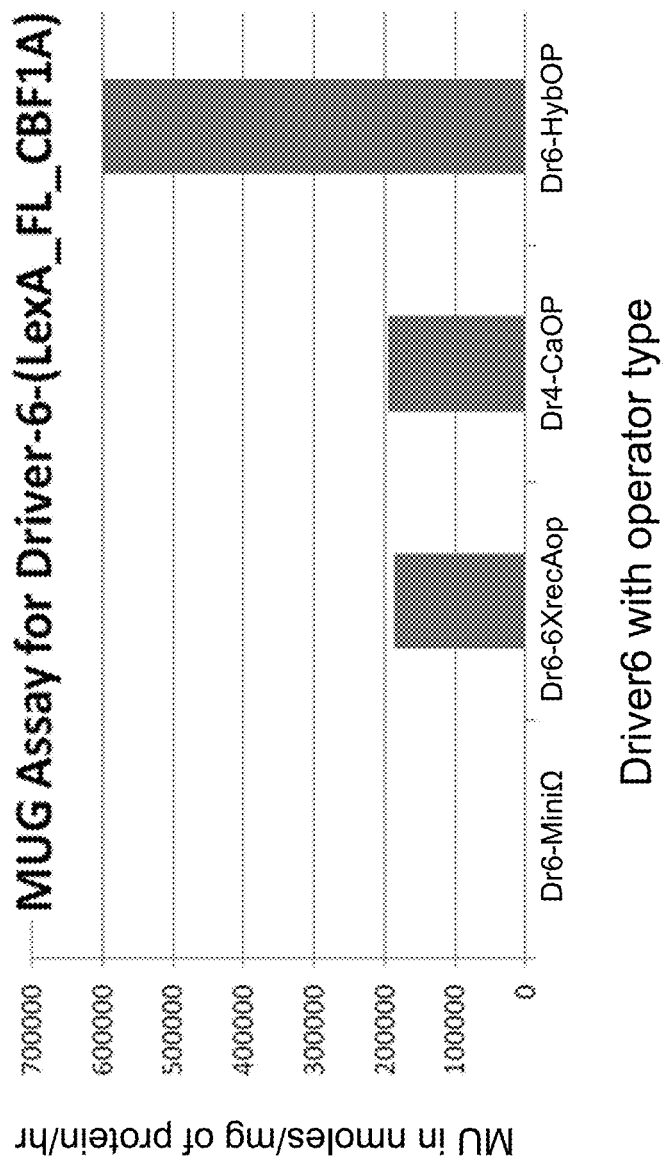
FIG. 5 shows the MUG analysis for Driver 6 with different operator combinations (Driver6 and 6×recA operator, Driver6 and 2×caa operator, Driver6 and hybrid operator) compared to the negative control (Driver6-miniΩ; no operator).

Results for MUG Assay for Operator::Driver-Transactivators:

MUG fluorescent assay data was analyzed for the positive samples from GUS assay which had shown GUS expression for the Driver4 (Table 11 and FIG. 4) and Driver6 (Table 12 and FIG. 5), with three operators combinations 6xRecAOP: MiniΩ::GUS, 2xCaaOP:MiniΩ::GUS, HybOP:MiniΩ::GUS and Negative Control_MiniΩ::GUS.

TABLE 11

MUG Fluorescent Assay Data for Driver4 with Different Operator Combinations

| Sample ID | MU readings | MU - bkg | MU in nmoles | MU in each well | Protein conc mg/ml | MU in nmoles/ mg of pro/hr |
|---|---|---|---|---|---|---|
| Dr4-MiniΩ | 62 | 0 | 0 | 0 | 1.33 | 0 |
| Dr4-6XRecAOP | 14621 | 14559 | 43.97 | 219.89 | 1.61 | 136174.10 |
| Dr4-2xCaaOP | 462 | 400 | 1.20 | 6.04 | 1.48 | 4078.99 |
| Dr4-HybOP | 3670 | 3608 | 10.89 | 54.48 | 1.53 | 35604.28 |

TABLE 12

MUG Fluorescent Assay Data for Driver6 with Different Operator Combinations

| Sample ID | MU readings | MU - bkg | MU in nmoles | MU in each well | Protein conc mg/ml | MU in nmoles/ mg of pro/hr |
|---|---|---|---|---|---|---|
| Dr6-MiniΩ | 90 | 0 | 0.00 | 0.00 | 1.17 | 0.00 |
| Dr6-6XRecAOP | 25070 | 24980 | 67.75 | 338.76 | 1.82 | 185819.53 |
| Dr6-2xCaaOP | 31997 | 31907 | 86.54 | 432.69 | 2.22 | 195036.26 |
| Dr6-HybOP | 72752 | 72662 | 197.08 | 985.39 | 1.65 | 598867.40 |

MU readings: Methylumbelliferone Readings
MU blanking: Methylumbelliferone blank sample Readings
MU in nmoles: Methylumbelliferone Readings in nanomoles
MU in each well: Methylumbelliferone Readings quantity in each well
Protein conc mg/ml: protein concentration in mg/ml of sample
MU in nmoles/mg of pro/hr: Methylumbelliferone in nanomoles per mg of protein per one hour incubation Example 5

Other Genes and Plant Species

The transactivation system described above can be used for regulating expression of other genes that can be used in place of GUS and may be used in other plant species such as rice, soybean and maize.

We claim:

1. A plant cell comprising:
   (a) a heterologous polynucleotide operably linked to a minimal promoter and a hybrid LexA operator sequence, wherein the hybrid LexA operator sequence comprises one copy each of at least two non-identical LexA operator sequences, wherein the hybrid LexA operator sequence comprises at least one sequence selected from the group consisting of: the polynucleotide of SEQ ID NO:22 and the polynucleotide of SEQ ID NO:23; and
   (b) a recombinant DNA construct comprising a promoter functional in a plant cell operably linked to a polynucleotide encoding a fusion protein, wherein the polynucleotide comprises:
      (1) a first nucleotide sequence encoding a first amino acid sequence having a DNA-binding domain wherein the first amino acid sequence is SEQ ID NO:36 or a functional fragment of SEQ ID NO: 36; and
      (2) a second nucleotide sequence encoding a second amino acid sequence having a transactivation domain wherein the second amino acid sequence is SEQ ID NO: 90 or a functional fragment of SEQ ID NO: 90, wherein the transactivation domain is operably linked to a nuclear localization sequence (NLS); wherein the fusion protein is capable of activating transcription of a heterologous polynucleotide that is operably linked to the hybrid LexA operator sequence.

2. The recombinant DNA construct of claim 1, wherein the heterologous polynucleotide encodes a heterologous polypeptide capable of modifying an agronomic characteristic in the plant cell.

3. The plant cell of claim 1, wherein the NLS in the recombinant DNA construct comprises the amino acid sequence encoded by the nucleotide sequence of SEQ ID NO:39.

4. The plant cell of claim 1, wherein the promoter in the recombinant DNA construct is a tissue-specific promoter.

5. The plant cell of claim 1, wherein the promoter in the recombinant DNA construct is an inducible promoter.

6. A plant obtained from the plant cell of claim 1.

7. A seed produced by the plant of claim 6, wherein said seed comprises said DNA construct and said heterologous polynucleotide.

8. A plant obtained from the plant cell of claim 4.

9. A seed produced by the plant of claim 8, wherein said seed comprises said DNA construct and said heterologous polynucleotide.

10. A method of regulating the expression of a heterologous polynucleotide in a plant, wherein the method comprises the steps of:
   a. obtaining a plant comprising: (i) a first recombinant DNA construct, where the first recombinant DNA construct is the recombinant DNA construct of claim 1; and (ii) a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; and
   b. growing the plant of step (a) under conditions in which the first recombinant DNA construct is expressed.

11. A method of regulating the expression of a heterologous polynucleotide in a plant, wherein the method comprises the steps of:
   a. obtaining a plant comprising a first recombinant DNA construct, where the first recombinant DNA construct is the recombinant DNA construct of claim 1;
   b. introducing into the plant of step (a) a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell; and
   c. growing the plant of step (b) under conditions in which the first recombinant DNA construct is expressed.

12. A method of regulating the expression of a heterologous polynucleotide in a plant, wherein the method comprises the steps of:
   a. introducing into a regenerable plant cell a first recombinant DNA construct, where the first recombinant DNA construct is the recombinant DNA construct of claim 1, and a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell;
   b. regenerating a transgenic plant from the regenerable plant cell of step (a) wherein the transgenic plant comprises in its genome the first recombinant DNA construct and the second recombinant DNA construct; and
   c. growing the transgenic plant of step (b) under conditions in which the first recombinant DNA construct is expressed.

13. A method of regulating the expression of a heterologous polynucleotide in a plant, wherein the method comprises the steps of:
   a. introducing into a regenerable plant cell a first recombinant DNA construct, where the first recombinant DNA construct is the recombinant DNA construct of claim 1, and a second recombinant DNA construct comprising a heterologous polynucleotide operably linked to a minimal promoter and at least one LexA operator sequence, wherein the heterologous polynucleotide encodes a heterologous polypeptide capable of modifying an agronomic characteristic in the plant cell;
   b. regenerating a transgenic plant from the regenerable plant cell of step (a) wherein the transgenic plant comprises in its genome the first recombinant DNA construct and the second recombinant DNA construct;
   c. obtaining a progeny plant derived from the transgenic plant of step (b), wherein the progeny plant comprises in its genome the first recombinant DNA construct and the second recombinant DNA construct; and
   d. growing the progeny plant of step (c) under conditions in which the first recombinant DNA construct is expressed.

14. The plant of claim 6, wherein the hybrid LexA operator sequence comprises at least one sequence of the polynucleotide of SEQ ID NO:22 and at least one sequence of the polynucleotide of SEQ ID NO:23.

15. The plant of claim 14, wherein the hybrid LexA operator sequence comprises more than one copy of the polynucleotide sequence of SEQ ID NO:22 or the polynucleotide sequence of SEQ ID NO:23.

16. The plant cell of claim 1, wherein the hybrid LexA operator sequence comprises at least one sequence of the polynucleotide of SEQ ID NO:22 and at least one sequence of the polynucleotide of SEQ ID NO:23.

17. The plant cell of claim 1, wherein the hybrid LexA operator sequence comprises more than one copy of the polynucleotide sequence of SEQ ID NO:22 or the polynucleotide sequence of SEQ ID NO:23.

* * * * *